(12) United States Patent
Edwards et al.

(10) Patent No.: US 11,298,014 B2
(45) Date of Patent: Apr. 12, 2022

(54) PHOTOBLEACHING METHOD

(71) Applicant: The UAB Research Foundation, Birmingham, AL (US)

(72) Inventors: John G. Edwards, Philadelphia, PA (US); Gregory R. Jackson, Hershey, PA (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 17/522,800

(22) Filed: Nov. 9, 2021

(65) Prior Publication Data

US 2022/0061657 A1    Mar. 3, 2022

Related U.S. Application Data

(63) Continuation of application No. 17/349,546, filed on Jun. 16, 2021, now Pat. No. 11,224,340, which is a (Continued)

(51) Int. Cl.
    *A61B 3/06*      (2006.01)
    *A61B 3/02*      (2006.01)
    *A61B 3/00*      (2006.01)

(52) U.S. Cl.
    CPC ............ *A61B 3/063* (2013.01); *A61B 3/0008* (2013.01); *A61B 3/0033* (2013.01); *A61B 3/022* (2013.01)

(58) Field of Classification Search
    CPC ..... A61B 3/063; A61B 3/0008; A61B 3/0033; A61B 3/022
(Continued)

(56) References Cited

U.S. PATENT DOCUMENTS

| 2,234,240 A | 3/1941 | Frohring |
| 8,795,191 B2 * | 8/2014 | Edwards ............... A61B 3/063 |
| | | 351/246 |

(Continued)

FOREIGN PATENT DOCUMENTS

WO    2005023094 A2    3/2005

OTHER PUBLICATIONS

Cideciyan, A. et al., 'Rod Plateaux During Dark Adaptation in Sorsby's Fundus Dystrophy and Vitamin A Deficiency', Investigative Opthalmology & Visual Science, vol. 38, No. 9, pp. 1786-1794 (1997).

(Continued)

*Primary Examiner* — Mohammed A Hasan
(74) *Attorney, Agent, or Firm* — White & Case LLP

(57) ABSTRACT

The present disclosure provides an improved method for photobleaching an eye of a subject. The disclosed method may be used in a number of psychophysical test methods, including, but not limited to, measurement of dark adaptation. The improved method for photobleaching involves at least one of the following improvements: (i) the use of a bleaching light emitting a particular wavelength of light or a tailored spectrum of wavelengths; (ii) restricting or otherwise spatially tailoring the region of the retina that is subject to photobleaching; and (iii) utilizing a bleaching light having an intensity that is at or below the intensity of ambient daylight. The present disclosure additionally provides a combination of a photobleaching light and an apparatus to administer a psychophysical test suitable for use in practicing the disclosed methods.

25 Claims, 12 Drawing Sheets

Related U.S. Application Data continuation of application No. 16/940,942, filed on Jul. 28, 2020, which is a continuation of application No. 14/451,077, filed on Aug. 4, 2014, now Pat. No. 10,779,722, which is a continuation of application No. 12/527,384, filed as application No. PCT/US2008/002095 on Feb. 15, 2008, now Pat. No. 8,795,191.

(60) Provisional application No. 60/890,131, filed on Feb. 15, 2007.

(58) Field of Classification Search
USPC .......................................................... 351/222
See application file for complete search history.

(56) References Cited

U.S. PATENT DOCUMENTS

| | | | |
|---|---|---|---|
| 10,779,722 B2 * | 9/2020 | Edwards | A61B 3/0008 |
| 2003/0004418 A1 | 1/2003 | Marmorstein | |
| 2004/0087843 A1 | 5/2004 | Rice et al. | |
| 2005/0010091 A1 | 1/2005 | Woods et al. | |
| 2005/0169662 A1 | 8/2005 | Ransom et al. | |
| 2006/0227290 A1 | 10/2006 | Murray et al. | |
| 2007/0121071 A1 | 5/2007 | Jackson et al. | |
| 2020/0352434 A1 * | 11/2020 | Edwards | A61B 3/0008 |

OTHER PUBLICATIONS

Curcio, Christine A., et al. "Human photoreceptor topography." Journal of Comparative Neurology 292.4: pp. 497-523 (1990).

Hecht, et al. The Dark Adaptation of Retinal Fields of Different Size and Location the Journal of General Physiology, pp. 321-337; (Nov. 20, 1935).

Jackson, G, et al., "Section 5 Aging and dark adaptation", Vision Research 39:23, pp. 3975-3982 (1999).

Lamb, T.D. "The Involvement of Rod Photoreceptors in Dark Adaptation" Vision Research; vol. 21; pp. 1773-1782 (1981).

Murray, Ian J. "Third Party Observation for application No. EP20040783299" European Patent Office; pp. 1-3 (Jan. 22, 2015).

Pugh, E.N., "Ruston's Paradox: Rod Dark Adaptation After Flash Photolysis", Vision Research Labotary, Universty of Michigan, Ann Arbor, Michigan (1974).

Schiefer, U, et al., "Clinical Neuro-Ophthalmology—A Practical Guide", Eds H. Wilheim and W. Hart; in: Springer, Chapter 7, "Electrophysiology" pp. 87-92 (2007).

Wolf, George, "The Discovery of the Visual Function of Vitamin A", J Nutr. Jun. 2001;131(6):1647-50.

\* cited by examiner

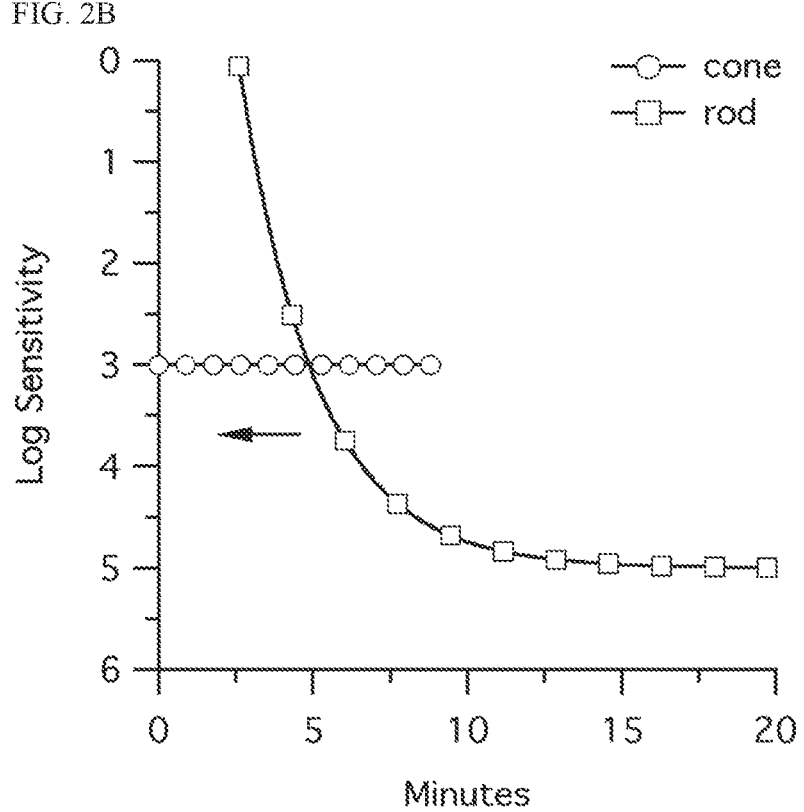

FIG. 5

All Subjects

| Subject | Sex | Race | Age | Correction | 1st Eye | 1st Color | White Flash | Green Flash | Difference | Green Preferred |
|---|---|---|---|---|---|---|---|---|---|---|
| 1 | m | white | 27 | contacts | right | white | 3 | 1 | 2 | yes |
| 2 | f | white | 22 | contacts | right | green | 8 | 5 | 3 | yes |
| 3 | f | white | 28 | none | right | white | 6 | 3 | 3 | yes |
| 4 | f | white | 24 | contacts | right | green | 8 | 4 | 4 | yes |
| 5 | f | white | 24 | contacts | right | white | 7 | 4 | 3 | yes |
| 6 | m | white | 24 | glasses | right | green | 6 | 2 | 4 | yes |
| 7 | m | white | 34 | none | right | white | 4 | 2 | 2 | yes |
| 8 | f | white | 42 | glasses | right | green | 5 | 3 | 2 | yes |
| 9 | m | white | 42 | glasses | right | white | 2 | 4 | -2 | no |
| 10 | f | white | 47 | glasses | right | green | 3 | 1 | 2 | yes |
| 11 | m | white | 23 | none | right | white | 4 | 2 | 2 | yes |
| Composite | | | 30.6 | | | | 5.1 | 2.8 | 2.3 | 91% |

If First Color was White

| Subject | Sex | Race | Age | Correction | 1st Eye | 1st Color | White Flash | Green Flash | Difference | Green Preferred |
|---|---|---|---|---|---|---|---|---|---|---|
| 1 | m | white | 27 | contacts | right | white | 3 | 1 | 2 | yes |
| 3 | f | white | 28 | none | right | white | 6 | 3 | 3 | yes |
| 5 | f | white | 24 | contacts | right | white | 7 | 4 | 3 | yes |
| 7 | m | white | 34 | none | right | white | 4 | 2 | 2 | yes |
| 9 | m | white | 42 | glasses | right | white | 2 | 4 | -2 | no |
| 11 | m | white | 23 | none | right | white | 4 | 2 | 2 | yes |
| Composite | | | 29.7 | | | | 4.3 | 2.7 | 1.7 | 83% |

If First Color was Green

| Subject | Sex | Race | Age | Correction | 1st Eye | 1st Color | White Flash | Green Flash | Difference | Green Preferred |
|---|---|---|---|---|---|---|---|---|---|---|
| 2 | f | white | 22 | contacts | right | green | 8 | 5 | 3 | yes |
| 4 | f | white | 24 | contacts | right | green | 8 | 4 | 4 | yes |
| 6 | m | white | 24 | glasses | right | green | 6 | 2 | 4 | yes |
| 8 | f | white | 42 | glasses | right | green | 5 | 3 | 2 | yes |
| 10 | f | white | 47 | glasses | right | green | 3 | 1 | 2 | yes |
| Composite | | | 31.8 | | | | 6.0 | 3.0 | 3.0 | 100% |

If Male

| Subject | Sex | Race | Age | Correction | 1st Eye | 1st Color | White Flash | Green Flash | Difference | Green Preferred |
|---|---|---|---|---|---|---|---|---|---|---|
| 1 | m | white | 27 | contacts | right | white | 3 | 1 | 2 | yes |
| 6 | m | white | 24 | glasses | right | green | 6 | 2 | 4 | yes |
| 7 | m | white | 34 | none | right | white | 4 | 2 | 2 | yes |
| 9 | m | white | 42 | glasses | right | white | 2 | 4 | -2 | no |
| 11 | m | white | 23 | none | right | white | 4 | 2 | 2 | yes |
| Composite | | | 30.0 | | | | 3.8 | 2.2 | 1.6 | 80% |

If Female

| Subject | Sex | Race | Age | Correction | 1st Eye | 1st Color | White Flash | Green Flash | Difference | Green Preferred |
|---|---|---|---|---|---|---|---|---|---|---|
| 2 | f | white | 22 | contacts | right | green | 8 | 5 | 3 | yes |
| 3 | f | white | 28 | none | right | white | 6 | 3 | 3 | yes |
| 4 | f | white | 24 | contacts | right | green | 8 | 4 | 4 | yes |
| 5 | f | white | 24 | contacts | right | white | 7 | 4 | 3 | yes |
| 8 | f | white | 42 | glasses | right | green | 5 | 3 | 2 | yes |
| 10 | f | white | 47 | glasses | right | green | 3 | 1 | 2 | yes |
| Composite | | | 31.2 | | | | 6.2 | 3.3 | 2.8 | 100% |

If Age under 30

| Subject | Sex | Race | Age | Correction | 1st Eye | 1st Color | White Flash | Green Flash | Difference | Green Preferred |
|---|---|---|---|---|---|---|---|---|---|---|
| 1 | m | white | 27 | contacts | right | white | 3 | 1 | 2 | yes |
| 2 | f | white | 22 | contacts | right | green | 8 | 5 | 3 | yes |
| 3 | f | white | 28 | none | right | white | 6 | 3 | 3 | yes |
| 4 | f | white | 24 | contacts | right | green | 8 | 4 | 4 | yes |
| 5 | f | white | 24 | contacts | right | white | 7 | 4 | 3 | yes |
| 6 | m | white | 24 | glasses | right | green | 6 | 2 | 4 | yes |
| 11 | m | white | 23 | none | right | white | 4 | 2 | 2 | yes |
| Composite | | | 24.6 | | | | 6.0 | 3.0 | 3.0 | 100% |

If Age over 30

| Subject | Sex | Race | Age | Correction | 1st Eye | 1st Color | White Flash | Green Flash | Difference | Green Preferred |
|---|---|---|---|---|---|---|---|---|---|---|
| 7 | m | white | 34 | none | right | white | 4 | 2 | 2 | yes |
| 8 | f | white | 42 | glasses | right | green | 5 | 3 | 2 | yes |
| 9 | m | white | 42 | glasses | right | white | 2 | 4 | -2 | no |
| 10 | f | white | 47 | glasses | right | green | 3 | 1 | 2 | yes |
| Composite | | | 41.3 | | | | 3.5 | 2.5 | 1.0 | 75% |

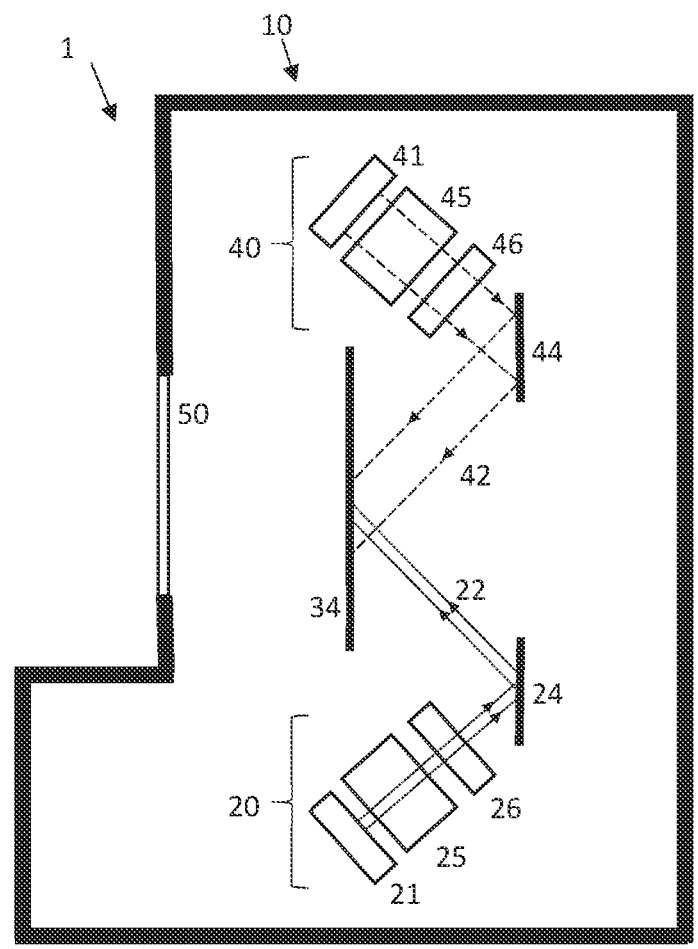

PHOTOBLEACHING METHOD

RELATED APPLICATIONS

This Application is a continuation of U.S. patent application Ser. No. 17/349,546, filed on Jun. 16, 2021, which is a continuation of U.S. patent application Ser. No. 16/940,942, filed on Jul. 28, 2020, which is a continuation of U.S. patent application Ser. No. 14/451,077, filed on Aug. 4, 2014 (now U.S. Pat. No. 10,779,722), which is a continuation of Ser. No. 12/527,384 filed on Mar. 4, 2010 (now U.S. Pat. No. 8,795,191), which is a 371 national stage filing of PCT International Application No. PCT/US2008/002095, filed on Feb. 15, 2008, which claims the benefit of and priority to U.S. Provisional Application No. 60/890,131, filed on Feb. 15, 2007. The specifications of each of the foregoing applications are hereby incorporated by reference in their entirety.

FIELD OF THE DISCLOSURE

The present disclosure relates to improved methods for photobleaching an eye, or a desired portion thereof, of a subject.

BACKGROUND

The retina is comprised of a thin layer of neural cells that lines the back of the eyeball of vertebrates. In vertebrate embryonic development, the retina and the optic nerve originate as outgrowths of the developing brain. Hence, the retina is part of the central nervous system. The vertebrate retina contains photoreceptor cells (both rods and cones) that respond to light; the resulting neural signals then undergo complex processing by neurons of the retina. The retinal output takes the form of action potentials in retinal ganglion cells whose axons form the optic nerve.

One component of the retina is the macula. The macula of the human eye, which is about 6 mm in diameter and covers the central 21.5 degrees of visual angle, is designed for detailed vision. The macula itself comprises a small cone-dominated fovea surrounded by a rod-dominated parafovea (Curcio 1990, J. Comp. Neurol. 292:497). Rods are responsible for vision in dim light (scotopic vision) while cones are responsive to bright light and colors (photopic vision). In young adults, the number of rods outnumbers cones by approximately 9:1. This proportion of rods to cones changes as individual's age.

The function of the rod and cone photoreceptors is impacted by the health of the rod and cone photoreceptors themselves. The health and function of the rod and cone photoreceptors are maintained by the retinal pigment epithelium (RPE), the Bruch's membrane and the choriocapillaris (collectively referred to as the RPE/Bruch's membrane complex). The RPE is a dedicated layer of nurse cells behind the neural retina. The RPE sustains photoreceptor health in a number of ways, including, but not limited to, maintaining proper ionic balance, transporting and filtering nutrients, providing retinoid intermediates to replenish photopigment bleached by light exposure and absorbing stray photons. The RPE and the photoreceptors are separated by the choriocapillaris, which provides blood flow to the neural retina. Further separating the RPE and the choriocapillaris is the Bruch's membrane, a delicate vessel wall only 2-6 μm thick.

The impairment of the rod and/or cone photoreceptors may lead to impairment in dark adaptation and other visual processes. Dark adaptation is defined as the recovery of light sensitivity by the retina in the dark after exposure to a conditioning light. In this regard, dark adaptation and other visual processes can essentially be viewed as a bioassay of the health of the rod photoreceptors, the RPE, the Bruch's membrane and the choriocapillaris, and impaired dark adaptation and the impairment of other visual functions may be used as a clinical marker of disease states that impair one or more of the rod and/or cone photoreceptors, the RPE, the Bruch's membrane and the choriocapillaris. For impairments in dark adaptation such disease states include, but are not limited to age-related macular degeneration (AMD; which is also known as age-related maculopathy ARM), vitamin A deficiency, Sorsby's Fundus Dystrophy, late autosomal dominant retinal degeneration, retinal impairment related to diabetes and diabetic retinopathy.

A subject's ability to dark adapt can be characterized by measuring scotopic sensitivity recovery (i.e., rod function) after photobleaching using psychophysical testing methods known in the art. In such psychophysical tests, typically a test eye of the subject is first pre-conditioned to a state of relative scotopic insensitivity by exposing the eye to a conditioning light (a procedure referred to as photobleaching or bleaching). After this pre-conditioning (or bleaching) step, the subject's scotopic sensitivity (the minimum light intensity that can be detected in a dark environment) is measured at one or more successive times. The measurement is made by exposing the bleached region of the test eye to a series of stimulus lights of varying intensities. Based on subject feedback as to which stimulus intensities can be detected, a sensitivity, or threshold, is determined for each successive time. The subject is kept in a dark environment throughout the test. The absolute levels and/or kinetics of the resulting threshold curve indicate the subject's ability to dark adapt. Impairment in the subject's dark adaptation parameters may indicate the subject is currently suffering from and/or at risk for a disease state that impairs one or more of the rod and/or cone photoreceptors, the RPE, the Bruch's membrane and the choriocapillaris.

The bleaching procedure is a critical element in the usefulness and utility of methods used to measure dark adaptation and in other psychophysical tests. Although it is well known that cones (the photoreceptors in the retina primarily responsible for photopic sensitivity) and rods (the photoreceptors in the retina primarily responsible for scotopic sensitivity) have different spectral response curves, existing photobleaching protocols used in psychophysical tests such as dark adaptation and dark adaptometers and other instruments used in such psychophysical tests invariably rely on white (achromatic) or very broadband light to achieve the desired photobleaching. Furthermore, all or a major portion of the retina area is photobleached, and the bleaching light intensity is set above ambient daylight (i.e., it has an intensity above the intensity of ambient daylight). The use of achromatic light, bleaching of all or a majority of the retina during the photobleaching process and the use of higher intensity bleaching lights can increase the duration of the psychophysical test, such as dark adaptation, can increase patient burden and discomfort during testing and can lead to greater test-to-test variation and/or measurement bias caused by variable lens opacity or other factors, with corresponding problems in interpretation of the psychophysical tests. The chromatic composition of the bleaching light, the portion of the retina area that is photobleached and the bleaching intensity can all have profound affects on the duration of the test, patient burden, test-to-test variability and measurement bias.

Therefore, the art is lacking an improved method of photobleaching for use with psychophysical tests, such as but not limited to, dark adaptation, and for use with instruments used in implementing such psychophysical tests. The present disclosure provides such an improved method of photobleaching, along with bleaching lights for use in the disclosed methods, and exemplary devices incorporating such bleaching lights and suitable for use in practicing the disclosed methods. Such disclosures were not heretofore appreciated in the art.

BRIEF DESCRIPTION OF THE FIGURES

FIG. 2B shows a theoretical illustration of a dark adaptation curve for a normal individual obtained using a photobleaching light emitting a range of wavelengths centered on 505 nm and a target stimulus of 505.

FIG. 5 shows the results of a preference test conducted comparing a photobleaching light emitting an achromatic white light comprising a broad wavelength spectrum of about 400 nm to about 700 nm and a bleaching light emitting a tailored spectrum of light consisting essentially of wavelengths of about 490 nm to about 510 nm (green spectrum).

FIG. 9A shows an internal side view of one embodiment of an apparatus combination for photobleaching a subject's eye.

DETAILED DESCRIPTION

General Description

Figure 1:
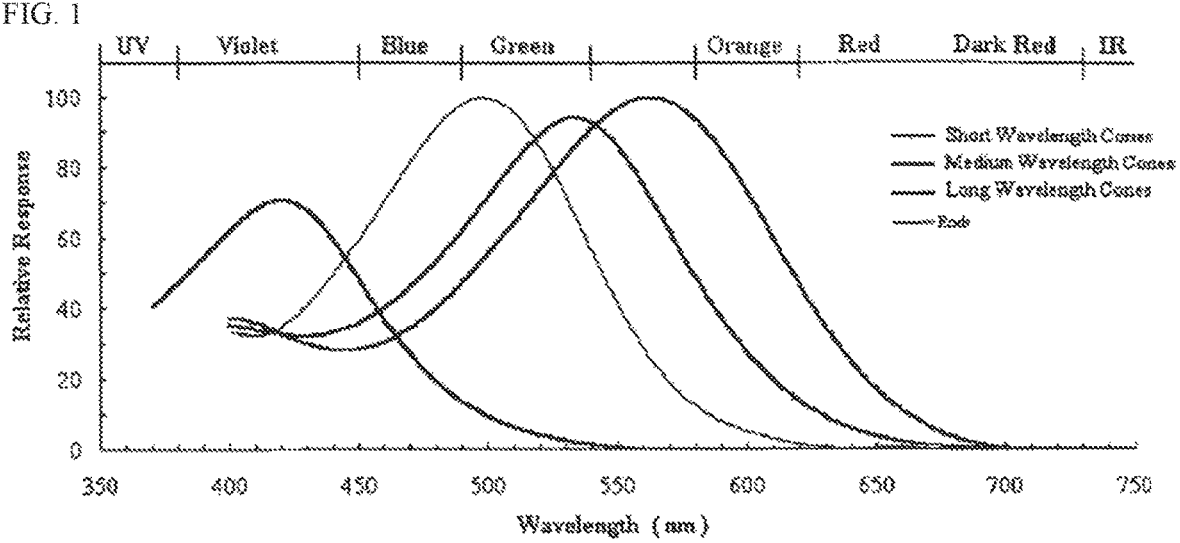
FIG. 1 shows various peak absorption profiles for the S, M and L cones and rod photoreceptors.

Rhodopsin and cone pigments are the visual pigments contained in the outer portions of the rod and cone photoreceptors of the retina, respectively. As the visual pigment absorbs light, it breaks down into intermediate molecular forms and initiates a signal that proceeds down a tract of nerve tissue to the brain, allowing for the sensation of sight. The outer segments of the rods and cones contain large amounts of these pigments, stacked in layers lying perpendicular to the light incoming through the pupil. There are five types of visual pigment in the retina, with slight differences that allow for differences in visual perception. Rhodopsin is the visual pigment in the rods and allows for scotopic vision. Rhodopsin in the rods absorbs light energy in a broad band of the electromagnetic spectrum peaking at 505 nm. There are three types of visual pigments in the cones, each with a slightly different peak absorption: short wavelength (S) cones have a spectral response peaking around 419 nm (the blue spectrum), medium wavelength (M) cones have a spectral response peaking around 531 nm (the green spectrum), and long wavelength (L) cones have a spectral response peaking around 558 nm (the red spectrum). The visual pigments in the cones allows for photopic vision. The various peak absorption profiles for the S, M and L cones and rod photoreceptors are shown in FIG. 1. Furthermore, about 1% of human retinal ganglion cells are photoreceptors. These light sensitive ganglion cells contain melanopsin photopigment, which have a spectral response peaking around 460 nm. These cells are thought to help regulate circadian photoentrainment. Depriving these ganglions cells of 460-nm light is hypothesized to disturb sleep/wake cycles in humans.

The following is a description of the biochemistry of rhodopsin, although the biochemistry of the cone pigments and melanopsin is thought to be very similar. Rhodopsin consists of 11-cis-retinal and the protein opsin, and is tightly hound in the outer segment of the rods, 11-cis-retinal is the photoreactive portion of rhodopsin, which is converted to all-trans-retinal when a photon of light in the active absorption band strikes the molecule. This process goes through a sequence of chemical reactions as 11-cis-retinal isomerizes to all-trans-retinal. During this series of chemical steps, the nerve fiber, which is attached to that particular rod or cone, undergoes a stimulus that is ultimately perceived in the brain as a visual signal. Following the breakdown of 11-cis-retinal to all-trans-retinal, the 11-cis-retinal is regenerated by a series of steps that result in 11-cis-retinal being recombined with opsin protein. The isomerization to all-trans-retinal is the reaction that occurs during the bleaching process.

The present disclosure provides an improved method for photobleaching an eye of a subject. The improved photobleaching process is achieved by using at least one of the following modifications to prior art bleaching protocols: (i) the use of a bleaching light emitting a particular wavelength of light or a tailored spectrum of wavelengths; (ii) restricting or otherwise spatially tailoring the region of the retina that is subject to photobleaching; and (iii) utilizing a bleaching light having an intensity that is at or below the intensity of ambient daylight. Such improvements to the prior art bleaching protocols for use in psychophysical tests, whether alone or in various combinations, have not been previously appreciated in the art. Likewise, instruments using the improved photobleaching methods and light source disclosed herein and improved instruments for administering psychophysical tests are also provided.

Using the improved photobleaching methods described herein, certain disadvantages associated with the prior art photobleaching methods are reduced or eliminated, resulting in a psychophysical test that is more efficient to administer and is shorter in duration. Furthermore, the patient burden and patient discomfort using the improved photobleaching method described herein is significantly reduced. Finally, the improved bleaching method described herein increases the accuracy and reproducibility of psychophysical tests by reducing test-to-test variation and measurement bias caused by pre-existing conditions. Therefore, such psychophysical tests are more accurate and easier to interpret.

The improved bleaching method described herein can be used in any psychophysical test or other testing procedure where photobleaching of a subject's eye is required. The present disclosure describes the use of the bleaching method disclosed in conjunction with measurements of dark adaptation as one example of application. However, the teachings of the present disclosure should not be limited to the use of the bleaching methods described to measurements of dark adaptation or any other single psychophysical test. The teachings of the present disclosure may be used in combination with any visual function test or any psychophysical test known in the art that requires bleaching the eye of the subject, or a portion thereof.

Psychophysical tests measure a subject's sensation and perception of physical stimuli. The stimuli can be visual, auditory, olfactory, tactile or gustatory. Visual stimuli include, for example, varying intensities of light, differing colors, and different sizes of text. Psychophysical tests using visual stimuli include, for example, dark adaptometry, visual sensitivity tests, spatial resolution acuity tests, contrast sensitivity tests, flicker photometry, photostress tests, Vernier acuity tests, colorimetry, motion detection tests, object recognition, and perimetry. Psychophysical tests can be used to assess the status of visual functions including, for example, dark adaptation, photopic sensitivity, scotopic sensitivity, visual acuity, color sensitivity, contrast sensitivity, color discrimination, and visual field. Psychophysical tests can be used to diagnosis the risk, presence or severity of eye diseases including, for example, age-related macular degeneration, vitamin A deficiency, Sorsby's fundus dystrophy, autosomal dominant late-onset degeneration, rod-cone dystrophies, color blindness, ocular tumors, cataract, diabetic retinopathy, and glaucoma.

The improved photobleaching methods described may be used in a variety of protocols, as would be obvious to one of ordinary skill in the art. As such, the exact protocol used with the described photobleaching methods may be varied as is known in the art. The goal of the photobleaching procedure in a psychophysical test (such as, but not limited to, dark adaptation) is to precondition the test eye of a subject, or portions thereof, by desensitizing at least a portion of the visual pigments of the test eye through exposure to a photobleaching light. In dark adaptation, for example, visual recovery of scotopic vision is then measured as the test eye adapts to a second light (often referred to as the target or target stimulus). Therefore, the photobleaching light serves as a standardized baseline from which visual recovery is measured. Therefore, the photobleaching step is of importance to psychophysical tests since it plays a role in establishing a baseline for the tests. Furthermore, depending on the nature of the photobleaching method used, the time required to complete the psychophysical test, the patient burden and patient discomfort, and the reproducibility and/or accuracy of the psychophysical test may be impacted.

In one embodiment for dark adaptation, the photobleaching light has a greater intensity than the target stimulus, but the absolute intensity values of the photobleaching light and the target stimulus may be varied as desired. Generally, the greater the absolute value of the intensity of the photobleaching light, the shorter the period of exposure of the test eye to the photobleaching light to achieve the baseline. For example, the photobleaching light may be an intense light, such as that provided by an electronic strobe or flash, and the light of the intensity of the target stimulus may be at or close to 0 $cd/m^2$, such as would occur in a dark room. Alternatively, the photobleaching light may be a light produced by an ordinary light bulb or by the ambient light in a room, and the intensity of the target stimulus may be at or close to 0 $cd/m^2$, such as would occur in a dark room. However, in general, the greater the intensity of the photobleaching light, the longer the psychophysical test takes to administer.

The wavelength of light emitted by the photobleaching light may also be varied. While the prior art methods utilized an achromatic bleaching light having a broad band spectrum of wavelengths, the present disclosure describes photobleaching methods that utilize a photobleaching light tailored to emit a light of a particular wavelength or a range of wavelengths of the visible spectrum so that light of only a particular wavelength or range of wavelengths is used in the bleaching process. In one embodiment, the particular wavelength or range of wavelengths is selected to match the specific absorption spectra of the rod, cone and/or retinal ganglion cell photoreceptors. As discussed above, rods absorb light in a broad band of the spectrum peaking at a wavelength of 505 nm, while the three types of cone photoreceptors have spectral responses peaking around 419 nm (S cones), around 531 nm (M cones), and around 558 nm (L cones) and the retinal ganglion cells absorb light having a spectral response peaking around 460 nm. Therefore, in one embodiment, the photobleaching light may be selected to stimulate one or more of the rod, cone and/or retinal ganglion cell photoreceptors by utilizing a photobleaching light emitting a wavelength or a range of wavelengths based on the spectral responses of the photoreceptors.

The photobleaching light emitting a particular wavelength or range of wavelengths of light may be generated by an achromatic light source equipped with a suitable filter, such as, but not limited to, a narrow-band pass filter, a high pass filter (eliminating lower wavelengths) or a low pass filter (eliminating the high wavelengths). A variety of narrow-band pass filters, high pass filters and low pass filters are commercially available and one of ordinary skill in the art would be well versed in the selection of the appropriate filter based on the test conducted and the results desired. Alternatively, the photobleaching light of a particular wavelength or range of wavelengths may be generated directly by a source generating the desired wavelength or wavelengths (such as, but not limited to, light emitting diodes, LEDs, or organic light-emitting diodes, OLEDs).

Many light delivery methods can be used to generate and/or deliver the photobleaching light. In one embodiment, the photobleaching light is generated by a xenon lamp, an arc lamp, a tungsten bulb, a photographic flash, a LED or OLED light source. Other possibilities include the use of display technologies such as cathode ray tubes (CRTs), plasma displays and LED displays. Other sources may also be used to generate the photobleaching light. As discussed above, the light sources may be equipped with filters or other devices to emit and/or generate light of a specific wavelength or range of wavelengths. The photobleaching light may be delivered using a variety of techniques as well, such as but not limited to, adapting fields, illuminated backgrounds, direct projection into the eye, exposure to ambient light, or staring into a light bulb. Classically, subjects viewed an adapting field in photobleaching methods. This bleaching method causes discomfort to the subject, and it is difficult to reliably deliver bleaches in psychophysically inexperienced subjects. Another method of bleaching is to project light into the eye using a Maxwellian view system. This method causes less irritation, but requires the subjects to fixate very steadily and not blink for 30 to 60 seconds. Many inexperienced subjects find this to be a difficult task. If the subject changes fixation or blinks, it is necessary to wait up to two hours before the bleach is repeated to avoid the cumulative effects of bleaching. Bleaching light delivered by an electronic strobe or flash delivers the photobleaching light in a short period of time. In addition, the intensity and/or wavelength or range of wavelengths emitted by the bleaching light may be easily modulated. In addition, the use of masks or similar devices allows the bleaching light to be of a desirable size and positioned at a desired location. Because the light exposure is brief, the intensity and/or wavelength(s) of the photobleaching light can be controlled and can be localized to a desired area, the photobleaching light is not irritating to the subjects and the subjects do not need to maintain fixation for a long period of time. With proper patient instructions blinking is not an issue.

The photobleaching light may be delivered to a desired portion of the retina. Using the delivery methods described above, it is possible to deliver the photobleaching light to a single discrete area of the retina or to more than one discrete area of the retina during a single test. By selecting a particular area or areas of the retina to be bleached by the photobleaching light, patient discomfort can be minimized by avoiding sensitive areas of the eye such as the fovea. In addition, depending on the goal of the test to be administered, a specific region of the retina may be selected for photobleaching. For example, when administering a psychophysical test for dark adaptation or other rod mediated function, it is not required to bleach the fovea since there are no rod photoreceptors in the fovea. Therefore, photobleaching a desired area or areas of the retina outside the fovea is advantageous. Finally, by photobleaching more than one discrete area of the retina, not only are the above mentioned advantages obtained, but in addition, different areas of the retina may be tested simultaneously to monitor disease progression and/or to get differential measurements from areas having or suspected of having greater or lesser dysfunction or to increase the statistical accuracy of the test results by providing more than one reading.

As discussed above, the photobleaching protocol desensitizes the desired amount of visual pigment in the rod, cone and/or retinal ganglion cell photoreceptors by exposure to a photobleaching light and provides a standardized baseline to measure visual recovery. The intensity of the photobleaching light, the time of exposure to the photobleaching light and/or the wavelength(s) of the photobleaching light can be modulated to produce the desired amount of desensitization as described herein. In one embodiment, an equivalent of about 50% to 100% of the visual pigment in the area subject to photobleaching is desensitized. The intensity of the photobleaching light can be adjusted to desensitize the appropriate amount of visual pigment in the area subject to photobleaching. For example, a photobleaching light intensity of 748 log scot Td $sec^{-1}$ will bleach approximately 98% of the rhodopsin molecules, while a photobleaching light intensity of 5.36 log scot Td $sec^{-1}$ will bleach approximately 50% of the rhodopsin molecules. Alternate photobleaching light intensities which desensitize less than 50% or more than 50% of the rhodopsin (or other visual pigment) molecules may also be used if desired.

After the bleaching protocol, visual recovery is monitored. In dark adaptation, for example, this recovery is mediated primarily by the retina and measures predominately rod-mediated scotopic sensitivity. Although many methods to monitor rod-mediated scotopic sensitivity are known, generally, the subject provides a series of responses to a target stimulus (which is varied in intensity, location and/or wavelength as described herein). In one method, the response of the subject is used to determine a threshold measurement. During threshold measurements, the subject is presented with a target stimulus. The target stimulus may be a spot of light, including a light spot on a darker background or a dark spot on a lighter background. Subjects may view the target stimulus with or without their best optical correction for the test distance. A variety of classical methods can be used to determine the threshold measurement, including but not limited to method of limits, just noticeable difference, and method of adjustment. These techniques are well known in the art. Thresholds measurements can be sampled in such a way as to provide sufficient data to fit models of dark adaptation. In one embodiment, threshold measurements are sampled once every 1 to 5 minutes. Another embodiment would be to sample threshold measurements twice every minute. Yet another embodiment would be to sample 2 threshold measurements per minute early during the test then sample 1 threshold measurement every 2 minutes thereafter. Higher or lower sampling rates may be used as desired to balance the need of producing an adequate dark adaptation function for model fitting against subject burden. As an example of lower sampling rates, a small number of threshold measurements may be sampled based on predictions of rod photoreceptor function in normal individuals. For example, a threshold measurement may be obtained at 3-5 minutes (which using classical photobleaching and target stimulus parameters in normal individuals would be before the rod-cone break) and at 5-10 minutes and 10-15 minutes. If these threshold measurements do not correlate with the rod photoreceptor function in normal individuals, the subject is likely to have impaired dark adaptation. Such a sampling schedule would further reduce subject burden. Additional description of methods and apparatus used in photobleaching methods and methods of analysis for determining the dark adaptation status of a patient are described in U.S. patent application Ser. No. 10/571,230, which is hereby incorporated by reference.

DESCRIPTION OF SPECIFIC EMBODIMENTS

In one embodiment of the photobleaching method described herein, the photobleaching light is tailored to emit a spectrum consisting essentially of a selected wavelength or range of wavelengths of light rather than an achromatic photobleaching light having a broad range of wavelengths. In many psychophysical tests, such as, but not limited to, dark adaptation, it may be advantageous to choose a photobleaching light tailored to emit a spectrum consisting essentially of a desired wavelength or a range of wavelengths that reveal the rod-mediated scotopic sensitivity as quickly as possible. Alternatively, it may be advantageous to choose a photobleaching light tailored to emit a spectrum consisting essentially of a desired wavelength or a range of wavelengths that provides a clearly visible rod-cone break as a characteristic benchmark for dark adaptation.

In a particular embodiment, the photobleaching light tailored to emit a spectrum consisting essentially of a desired wavelength or a range of wavelengths selected to preferentially photobleach the rod photoreceptors, the cone photoreceptors and/or retinal ganglion cells. For example, the photobleaching light may be selected to preferentially bleach the rod photoreceptors. In such an example, the photobleaching light would emit a spectrum consisting essentially of a wavelength of light of 505 nm or a range of wavelengths of light centered on 505 nm. As used herein, the term "centered" on a particular wavelength means the photobleaching light contains the particular wavelength of light and a range of other wavelengths of light from 5 to 20 nm on either side of the particular wavelength; the term centered should not be interpreted to mean the range of wavelengths is symmetrical about the particular wavelength. In the above example, light consisting essentially of a range of wavelengths centered on 505 nm could include, for example, wavelengths of light from 490 to 520 nm (15 nm on either side of 505 nm), from 490 to 510 nm, or from 490 to 525 nm. In another example, the photobleaching light may be selected to preferentially bleach the S cones photoreceptors. In such an example, the photobleaching light would emit a spectrum consisting essentially of a wavelength of light of 419 nm or a range of wavelengths of light centered on 419 nm. In yet another example, the photobleaching light may be selected to preferentially bleach the M and L cone photoreceptors while leaving the rod photoreceptors relatively unaffected. In such an example, the photobleaching light would emit a spectrum consisting essentially of a wavelength of light of 650 nm or a range of wavelengths of light centered on 650 nm, or alternately a broad range of wavelengths of light from about 600 nm to about 700 nm.

Other embodiments may also be envisioned. For example, when desired to preferentially bleach the visual pigment in the retinal ganglion cells, the photobleaching light may be tailored to emit a spectrum consisting essentially of a wavelength of light of 460 nm or a range of wavelengths of light centered on 460 nm, such as but not limited to, about 450 to about 470 nm.

In a further example, the photobleaching light may be tailored to emit a spectrum consisting essentially of a wavelength of light or a range of wavelengths of light over about 480 nm. Such a spectrum of photobleaching light may be used to exclude wavelengths of light in the blue spectra to reduce variability and confounding effects introduced by lens opacity.

In yet another example, the photobleaching light may be tailored to emit a spectrum consisting essentially of a wavelength of light of about 410 nm or centered on 410 nm, such as but not limited to a range of about 400 to about 420 nm. Such a spectrum of photobleaching light may be used to maximize absorption due to lens opacity.

In still a further example, the photobleaching light may be tailored to emit a spectrum consisting essentially of a wavelength of light of about 570 nm or centered on 570 nm, such as but not limited to a range of about 560 to about 580 nm. Such a spectrum of photobleaching light may be used to minimize absorption due to lens opacity.

In yet another example, when a target stimulus is used, the photobleaching light may be tailored to emit a spectrum that matches the spectrum of the target stimulus. When it is desired to accentuate the rod response, the spectrum of the photobleaching light and the target stimulus may be tailored to emit a spectrum consisting essentially of a wavelength of light of about 500 nm or centered on 500 nm, such as but not limited to a range of about 490 to about 510 nm. When it is desired to accentuate the cone response, the spectrum of the photobleaching light and the target stimulus may be tailored to emit a spectrum consisting essentially of a wavelength of light of about 650 nm or centered on 650 nm, such as but not limited to a range of about 640 to about 660 nm. In a further variation, the photobleaching light may be tailored to emit a spectrum that does not match the spectrum of the target stimulus.

In one version of this embodiment, rather than utilizing an achromatic or broadband bleaching light, a dark adaptometer can be configured to preferentially photobleach the rods. This could be accomplished, for example, by placing a band pass filter narrowly centered on 505 nm over a broadband xenon arc flash or other light source and using the resulting narrow spectrum emitted light as the bleaching source. Alternatively, the bleaching light could be configured to preferentially photobleach rods by constructing a bank of one or more light-emitting diodes (LEDs), organic light-emitting diodes (OLEDs) or other light source of a single type having a characteristic emission spectrum close to 505 nm. Other possibilities include the use of display technologies such as cathode ray tubes (CRTs), plasma displays and LED displays. Utilizing a bleaching spectrum that is tailored to preferentially photobleach the rods offers several advantages. Therefore, the photobleaching light is tailored to emit a light consisting essentially of a desired wavelength or range of wavelengths of light.

As discussed above, the photobleaching light emitting a desired wavelength or spectrum of wavelengths may be generated using a variety of methods. For example, a light source equipped with a suitable filter, such as, but not limited to, a narrow-band pass filter, a high pass filter (eliminating lower wavelengths) or a low pass filter (eliminating the high wavelengths). A variety of narrow-band pass filters, high pass filters and low pass filters are commercially available and one of ordinary skill in the art would be well versed in the selection of the appropriate filter based on the test conducted and the results desired. Alternatively, the photobleaching light of a particular wavelength or range of wavelengths may be generated directly by a source generating the desired wavelength or wavelengths (such as, but not limited to, light emitting diodes, LEDs, or organic light-emitting diodes, OLEDs).

Figure 2A:
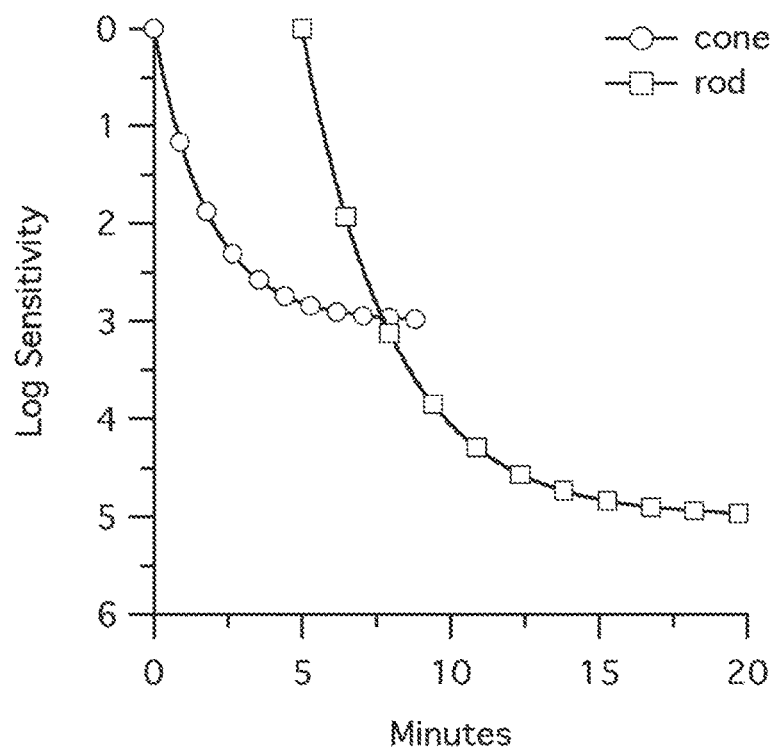
FIG. 2A shows a theoretical illustration of a dark adaptation curve for a normal individual obtained using a broad, achromatic photobleaching light and a 505 nm stimulus target.

Using a photobleaching method incorporating a photobleaching light tailored to emit a desired wavelength or range of wavelengths has several advantages. A first advantage is the ability to administer a psychophysical test, such as, but not limited to, dark adaptation, in a decreased amount of time, thereby increasing the efficiency of the test operator and minimizing patient burden. When an achromatic or broadband bleaching light is utilized in a photobleaching method, all of the photoreceptors, both rod and cone, are strongly bleached. Cones recover more rapidly than rods. Nevertheless, during the initial post-bleach period the sensitivity threshold is still dominated by the cone recovery, and the important rod-mediated scotopic sensitivity recovery information is obscured. However, using a photobleaching method incorporating a photobleaching light tailored to emit a desired wavelength or range of wavelengths can minimize the bleaching of photoreceptors whose function is not being tested. For example, using a bleaching light consisting essentially of a wavelength of light of 505 nm or centered on 505 nm, the photobleaching of the three cone photoreceptors is minimized and they are only weakly photobleached. As a result, the cones recover more rapidly, and the important rod-mediated scotopic sensitivity recovery information is more quickly revealed (see FIG. 2.) FIG. 2A is a theoretical illustration of a dark adaptation curve for a normal individual obtained using a broad, achromatic photobleaching light and a 505 nm stimulus target. Cone recovery and rod recovery are both exponential. Scotopic sensitivity is cone-mediated until the cone recovery plateaus to reveal the ultimately more sensitive rod-mediated response. FIG. 2B is a theoretical illustration of a dark adaptation curve for a normal individual obtained using a photobleaching light emitting a range of wavelengths centered on 505 nm and a target stimulus of 505. The cone recovery reaches its plateau essentially instantaneously and the rod recovery is more rapid than for the conditions of FIG. 2A, more quickly reaching the rod-cone break and revealing the subsequent rod-mediated recovery.

A second advantage is reduced patient burden during the test. Visual discomfort from bright lights is mainly associated with the short wavelength portion of the visible spectrum. As illustrated in Example 2, using a photobleaching light having a wavelength of 505 nm or a spectrum of wavelengths centered on 505 nm reduces patient burden by eliminating the most irritating short wavelength components of the light. Furthermore, the cone photobleaching associated with an achromatic or broadband photobleaching light creates a more persistent after image, which in turn causes the light of the target stimulus to be less salient and makes the test more difficult for the patient.

A third advantage is reduced measurement bias due to variation in the lens opacity of the patient. With aging or in the event of cataracts, the lens in the eye becomes more opaque and preferentially absorbs light at short wavelengths (i.e., 480 nm and below). With an achromatic or broadband bleaching light that contains a significant short wavelength component, variable lens density between otherwise similar subjects causes variability in the photobleaching achieved, and in turn an artificial variability in the measured dark adaptation. By using a photobleaching light tailored to emit a desired wavelength or spectrum of wavelengths that do not contain the shorter wavelengths, such variability is reduced.

Using a photobleaching method incorporating a narrow-band pass photobleaching light other than 505 nm or a range of wavelengths centered on 505 nm will minimize or maximize the degree of the above described advantages, depending on the wavelength or range of wavelengths chosen. In addition, at least some of the advantages described above (such as lowered patient burden and reduced bias due to lens opacity) can be obtained by use of a high pass filter to eliminate the short wavelength portion of the photobleaching spectrum rather than a narrow-band pass filter, although a narrow-band pass filter may also be used.

Figure 3A:
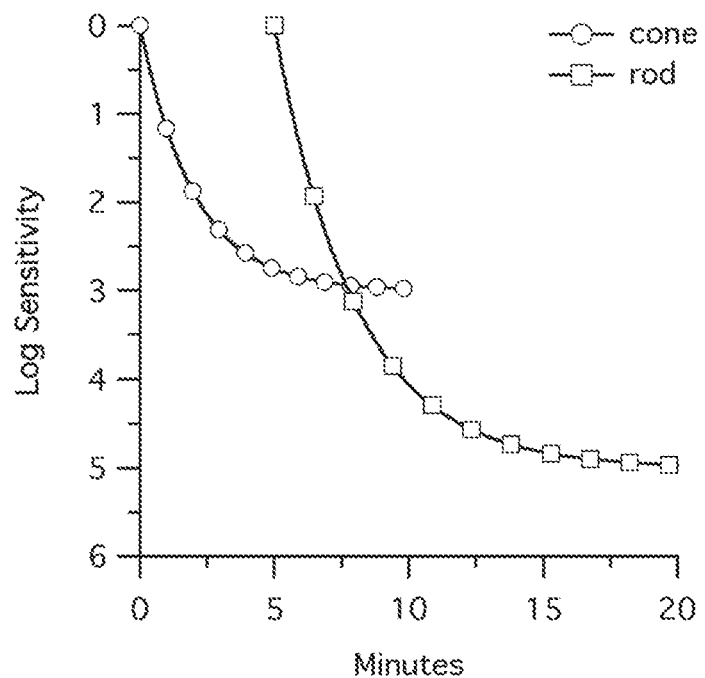
FIG. 3A shows a theoretical illustration of a dark adaptation curve for a normal individual obtained using a broad, achromatic bleaching light and a 505 nm target stimulus.
Figure 3B:
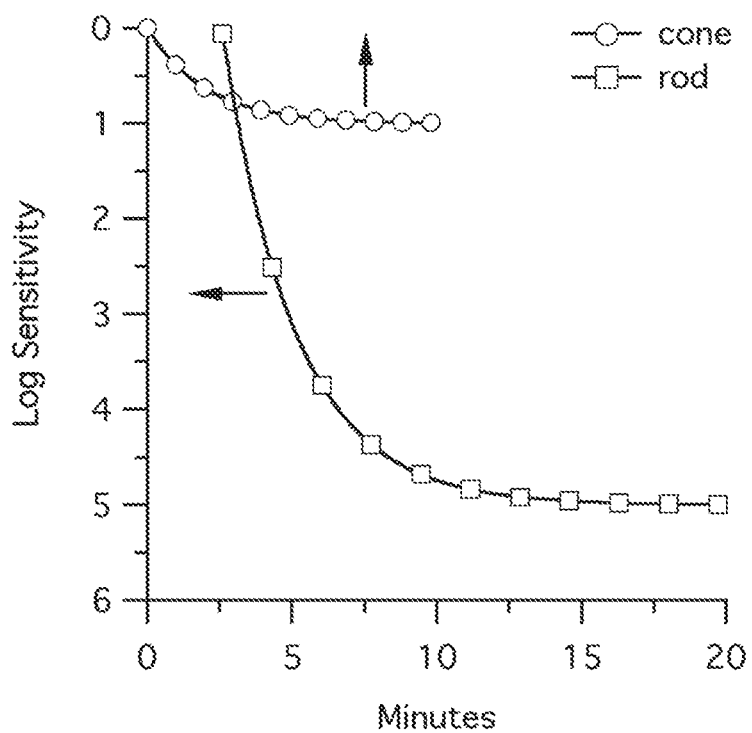
FIG. 3B shows a theoretical illustration of a dark adaptation curve for a normal individual obtained using a photobleaching light emitting a range of wavelengths centered on 560 nm and a stimulus target centered on 450 nm.

In yet another embodiment, further advantage may also be obtained using a photobleaching method utilizing a photobleaching light tailored to emit a desired wavelength or spectrum of wavelengths selected to complement a target stimulus of a specific wavelength(s) of light. For example, by combining a photobleaching light consisting essentially of a wavelength of light of 560 nm or a range of wavelengths of light centered on 560 nm with a target stimulus consisting essentially of a wavelength of light of 450 nm or a range of wavelengths of light centered on 450 nm, it is possible to obtain a rapid assessment of the rod-mediated scotopic sensitivity recovery (i.e., dark adaptation). Such a photobleaching light will only weakly photobleach the S cones, but will strongly photobleach the M and L cones as well as the rods. Conversely, all of the S, M and L cones as well the rods are strongly responsive to such a target stimulus. Given this combination, during the initial portion of the rod-mediated scotopic sensitivity recovery the S cone response will dominate the M and L cone responses, and rapidly saturate at the short wavelength cone plateau until the ultimately more sensitive rods take over. This provides a clear rod-cone break (the point at which sensitivity recovery transitions from being cone dominated to being rod dominated) in the threshold curve. An illustration is provided in FIGS. 3A and B. FIG. 3A is a theoretical illustration of a dark adaptation curve for a normal individual obtained using a broad, achromatic bleaching light and a 505 nm target stimulus. Cone recovery and rod recovery are both exponential. Scotopic sensitivity is cone-mediated until the cone recovery plateaus to reveal the ultimately more sensitive rod-mediated response. FIG. 3B is a theoretical illustration of a dark adaptation curve for a normal individual obtained using a photobleaching light emitting a range of wavelengths centered on 560 nm and a stimulus target centered on 450 nm. The cone recovery plateaus at a higher level and the rod recovery is more rapid than for the conditions of FIG. 3A, more quickly reaching the rod-cone break and revealing the subsequent rod-mediated recovery.

In an alternate embodiment of the photobleaching method described herein, the bleaching light is restricted to a portion of the retina so that only a portion of the retina is photobleached. The area of the retina to be photobleached may be selected based on the particular test to be administered, the results desired, or the nature of the photoreceptors desired to be photobleached; furthermore, the area of the retina to be photobleached may be selected in order to maximize diagnostic sensitivity for a particular disease and/or to minimize patient burden. A combination of the above factors may also suggest certain portions of the retina to be photobleached. The positioning of the bleaching light to a desired area of the retina can be accomplished, for example, by an appropriately located and sized mask over the bleaching light or the bleaching light could be projected onto only the desired region of the retina. In addition, a fixation light or other element and/or a restraint, such as, but not limited to, a chin rest or bite bar, could be used in combination with the foregoing to orient the patient's retina to allow precise placement of the bleaching light on a desired portion of the retina.

In a particular embodiment, in a psychophysical test for dark adaptation, it may be beneficial to restrict application of the bleaching light to an area of the parafovea and avoid application of the bleaching light to the fovea. Application of the bleaching light to the fovea causes greater irritation than light directed at regions of the retina outside the fovea, such as, but not limited to, the parafovea. Furthermore, there are no rod photoreceptors in the fovea, so bleaching the fovea will not contribute to assessment of rod-mediated function.

In addition, some diseases that are associated with impaired dark adaptation exhibit greater or lesser impairment depending on the region of the retina tested. In the case of age-related macular degeneration, for example, AMD-related impairment of the rods is greatest near the fovea and decreases as a function of eccentricity towards the peripheral retina. It is therefore possible to monitor disease progression by determining the patient's dark adaptation status at several points of the retina as a function of eccentricity towards the peripheral retina. Therefore, by selectively photobleaching only desired areas of the retina with different degrees of eccentricity, the progression of certain diseases can be monitored. In such embodiments, several areas of the retina with different degrees of eccentricity can be photobleached at one time, with the patient's dark adaptation status being determined for each region of the retina that is photobleached, for example by interleaving threshold measures at the multiple regions. As is obvious, the different regions of the retina could also be studied independently in completely separate tests.

In a particular embodiment suitable for the testing of dark adaptation, the region of the retina that is photobleached is restricted to a small focal area equal to 4° of visual field centered at 5° in the inferior visual field (in the macula but outside the fovea), with this beaching region being only moderately larger than the target stimulus light spot. This choice of bleaching region offers several advantages. For one, patient burden is minimized, both because the fraction of the retina being photobleached is small and because the region selected excludes the fovea, which is the portion of the retina most susceptible to irritation. Avoiding the fovea also allows the patient to maintain fixation easier during the test, which is critical for test reliability. For another, diagnostic sensitivity for AMD is optimized, because AMD-related impairment of dark adaptation is greatest in this region of the retina.

In other embodiments, the photobleaching light photobleaches a portion of the retina as set forth below.

In one example, the portion of the retina exposed to the photobleaching light is an area of the fovea, an area of the parafovea or a combination of the foregoing. The portion of the retina exposed to the photobleaching light may be located entirely inside the fovea (at about 0° to about 0.5° eccentricity). Such localization would allow photobleaching primarily of the cone photoreceptors and may be useful in such psychophysical tests as color sensitivity or color discrimination. The portion of the retina exposed to the photobleaching light may be located entirely inside the macula (at about 2° to about 10° eccentricity or at about 3° to about 10° eccentricity). Such localization would allow photobleaching primarily of the rod photoreceptors and may be useful in such psychophysical tests as dark adaptation. Furthermore, the portion of the retina exposed to the photobleaching light may be located in the peripheral retina (at about 10° to about 30° eccentricity). Such localization may be useful in such psychophysical tests as visual field or perimetry.

In another example, the portion of the retina exposed to the photobleaching light may be an annular region completely excluding the fovea. In a specific example, the annular region may have an inner edge located at or outside about 2° eccentricity and an outer edge located at or inside about 10° eccentricity. Such localization would allow primarily bleaching of the rod photoreceptors as discussed above.

In a further example, the portion of the retina exposed to the photobleaching light covers an area of about 4° of visual field to about 6° of visual field. Such an area allows a minimum effective area of the retina to be exposed to photobleaching while providing a photobleached area that can be effectively exposed to the target stimulus. In another example, the portion of the retina exposed to the photobleaching light is co-located with the portion of the retina exposed to the target stimulus and the portion of the retina exposed to the bleaching light being from about 1 to about 4 times the area of the portion of the retinal exposed to the target stimulus. In a specific example, the portion of the retina exposed to the photobleaching light is about 3 times the area of the portion of the retinal exposed to the target stimulus.

In still a further example, the portion of the retina exposed to the photobleaching light is located on the inferior vertical meridian or the superior vertical meridian. Such localization allows for symmetry between the right and left eye.

In yet another example, the portion of the retina exposed to the photobleaching light has a distinctive shape. In certain cases, the photobleaching process may produce an after image. When a target stimulus is used, such as in conjunction with a psychophysical test, the subject may confuse the after image with the target stimulus. By providing a distinctive shape to the photobleaching light such confusion is minimized. The shape may be a circle, a square, a triangle, a diamond, a polygon, a star or other shape as desired. In a specific example, the photobleaching light and the target stimulus have different shapes. If desired, color may be substituted for shape, or both color and shape may be used.

In yet another alternate embodiment of the photobleaching method described herein, the photobleaching method utilizes a bleaching light with an intensity that is at or below the intensity of ambient daylight levels. For the purpose of this disclosure, the intensity of ambient daylight is in the range of 50 to 400 cd/m$^2$ or 3.15 to 4.05 log scot Td sec$^{-1}$. Prior photobleaching methods and devices utilizing such methods, especially those used for measuring dark adaptation, utilized a photobleaching light having an intensity that was well above the intensity of ambient daylight. This brute force approach was used to ensure a uniform state of photobleaching, or adaptation starting point, for all patients. However, it is also possible to ensure a uniform state of photobleaching with a photobleaching light having an intensity that is at or below the intensity of ambient daylight. For example, the patient can be taken from ambient daylight into a dark room, allowed to dark adapt briefly to a level below ambient daylight, and then photobleached using a flash of light having an intensity at or below the intensity of ambient daylight. Alternatively, the patient can be taken from ambient daylight into a dark room, exposed to a steady photobleaching light having an intensity below the intensity of ambient daylight until such time as the steady photobleaching light is clearly visible to the patient, thus effectively arresting dark adaptation for all patients at a common starting level below ambient daylight conditions. In the latter alternative, the steady photobleaching light can be a randomly selected shape that the patient must identify to the test operator before dark adaptation testing can proceed, thereby verifying that the patient is appropriately pre-conditioned. Use of a photobleaching light with an intensity that is at or below the intensity of ambient daylight levels offers several advantages. In particular, the patient burden is reduced. In addition, as illustrated in Example 4 below, the overall dark adaptation test time can be shortened.

The described photobleaching methods may utilize one, two or all three of the above described improvements, in any combination. For example, a photobleaching method may be provided using a photobleaching light emitting a light consisting essentially of a specific wavelength of light or a tailored spectrum of wavelengths centered on a specific wavelength of light. In another example, a photobleaching method may be provided using a photobleaching light emitting a light consisting essentially of a specific wavelength of light or a tailored spectrum of wavelengths centered on a specific wavelength of light in combination with only a particular area of the retina photobleached. In yet another example, a photobleaching method may be provided using a photobleaching light having an intensity that is at or below the intensity of ambient daylight.

Furthermore, the described photobleaching methods may also be incorporated into an apparatus, machine or device used to administer a psychophysical test that requires photobleaching, such as, but not limited to a dark adaptometer. Such apparatus, machines or devices are well known in the art and may be modified to incorporate the photobleaching methods described herein. Such a modified apparatus, machine or device is also within the scope of the present disclosure. For example, the dark adaptometer disclosed in U.S. Pat. No. 10/571,230 could be modified to incorporate the photobleaching methods described herein. Likewise, a photobleaching light source capable of emitting a tailored range of wavelengths or a particular wavelength suitable to photobleach a desired population of rod, cone or ganglion cell photoreceptors or a photobleaching light emitting a light having an intensity at or below the intensity of ambient daylight are also within the scope of the disclosure, as well as the use of such photobleaching light sources in an apparatus, machine or device used to administer a psychophysical test that requires photobleaching.

The present disclosure also provides a combination of a photobleaching light as described herein and an apparatus to administer a psychophysical test to monitor a response to the photobleaching light. The photobleaching light may be a part of the apparatus. As discussed above, the nature of the apparatus may be determined by the psychophysical test administered. For example, dark adaptometers (or biophotometers) are used to measure dark adaptation and diagnose age-related macular degeneration, preferential hyperacuity perimeters are used to measure Vernier acuity and assess the severity of age-related macular degeneration, ETDRS charts are used to measure spatial resolution acuity, Pelli-Robson contrast sensitivity charts are used to measure contrast sensitivity, the Farnsworth-Munsell 100 Hue Test is used to measure color vision, frequency doubling perimeters are used to measure frequency doubling visual illusion, and field analyzers are used to measure visual field and diagnose glaucoma.

Figure 9B:
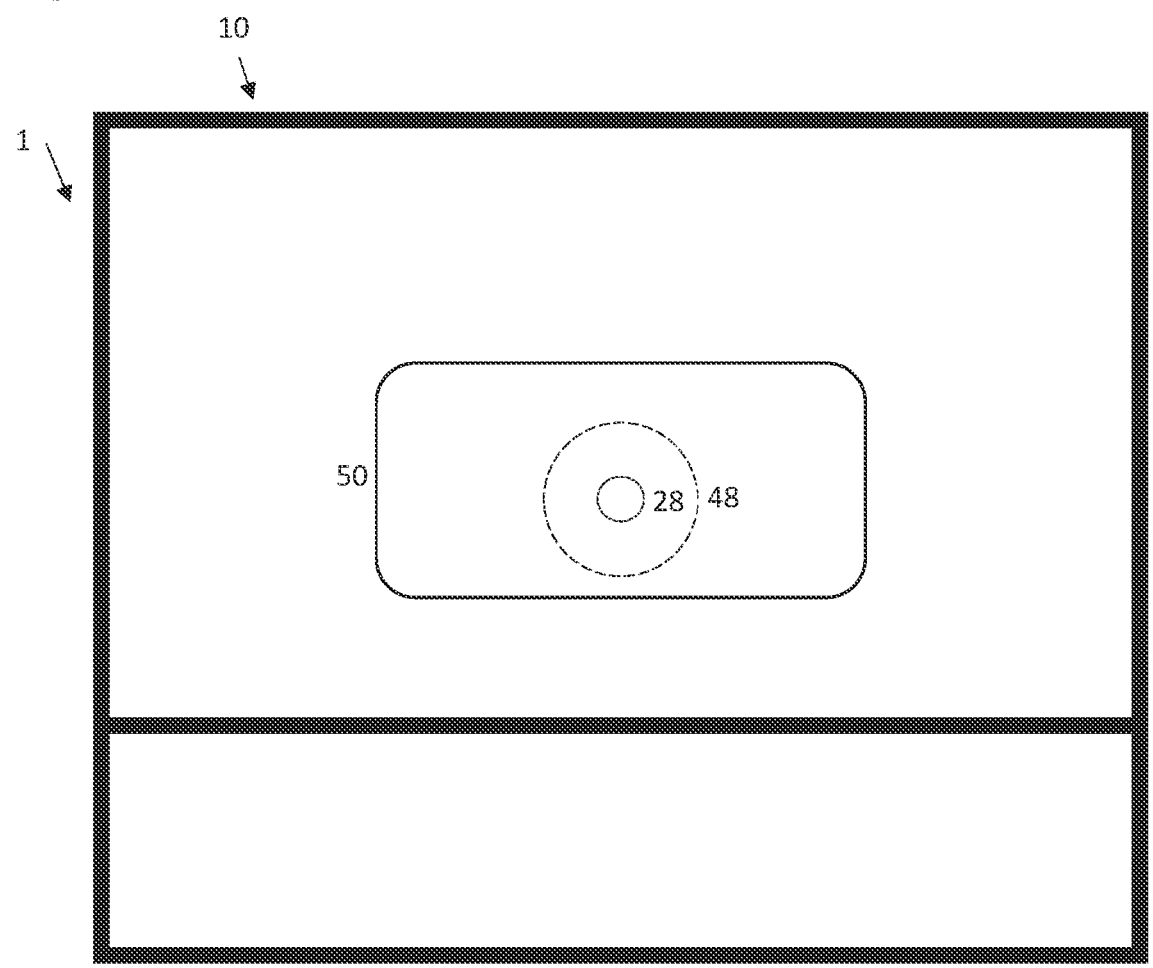
FIG. 9B shows a front view of the apparatus combination of FIG. 9A.

An exemplary apparatus combination is shown in FIGS. 9A and 9B. The apparatus combination 1 (i.e., a dark adaptometer) comprises a housing 10. The housing 10 has a viewing opening 50 to receive the head of the subject being tested. The housing 10 contains the basic components of the apparatus combination 1, including in particular a photobleaching apparatus 40 for photobleaching a restricted region of a retina of a subject's eye and a stimulus apparatus 20 for exposing a desired portion of a retina of a subject's eye to a target stimulus light.

In one embodiment, the photobleaching apparatus 40 includes a bleaching light source 41 (for example one of more LEDs) to generate a bleaching light beam 42. The bleaching light source 41 may be adjusted to provide a high intensity or a low intensity beam. The bleaching light beam 42 is acted on by one or more optical elements, including for example shaping optics 45 to collimate and shape the beam (for example a mask with an appropriately sized aperture or a series of lenses), an optical filter 46 to select the desired spectrum of the beam 42, and a directing means 44 (for example a mirror) to direct the beam to a display 34 (for example a screen). These elements combine to produce a bleaching spot 48 (FIG. 9B) of the desired size, shape and spectrum of light on the display 34 to photobleach at least a portion of rod visual pigment in only a restricted region of a retina of the subject's eye.

In one embodiment, the stimulus apparatus 20 includes a stimulus light source 21 (for example one or more LEDs) to generate a stimulus light beam 22. The stimulus light source 21 may be adjusted to control the intensity of the stimulus light bean 22 over a broad dynamic range. The stimulus light source 21 is acted one by one or more optical elements, including for example shaping optics 25 to collimate and shape the beam (for example a mask with an appropriately sized aperture or a series of lenses), an optical filter 26 to select the desired spectrum of the beam 22, and a directing means 24 (for example a mirror) to direct the beam to the display 34 (for example a screen). These elements combine to produce a target stimulus spot 28 (FIG. 9B) of the desired size, shape and spectrum of light on the display means 34 so that only a portion of a retina of the subject's eye is exposed to the target stimulus.

Psychophysical tests using visual stimuli include, for example, dark adaptometry, visual sensitivity tests, spatial resolution acuity tests, contrast sensitivity tests, flicker photometry, photostress tests, Vernier acuity tests, colorimetry, motion detection tests, object recognition, and perimetry. The combination can be used to assess the status of visual functions including, for example, dark adaptation, photopic sensitivity, scotopic sensitivity, visual acuity, color sensitivity, contrast sensitivity, color discrimination, and visual field. Furthermore, the combination can be used to diagnosis the risk, presence or severity of eye diseases including, for example, age-related macular degeneration, vitamin A deficiency, Sorsby's fundus dystrophy, autosomal dominant late-onset degeneration, rod-cone dystrophies, color blindness, ocular tumors, cataract, diabetic retinopathy, and glaucoma.

EXAMPLES

Example 1—Effect of Photobleaching Light Spectrum on the Shape and Kinetics of Dark Adaptation Curves In this example, a comparison was made between dark adaptation curves generated using a photobleaching light emitting an achromatic white light comprising a broad spectrum of wavelengths and dark adaptation curves generated using a photobleaching light emitting a tailored spectrum of wavelengths centered on only the blue, green and red portions of the achromatic white photobleaching light.

Dark adaptation was measured using an AdaptDx dark adaptometer (Apeliotus Technologies, Inc.) according to the manufacturer's instructions, using methods known in the art.

Figure 4A:
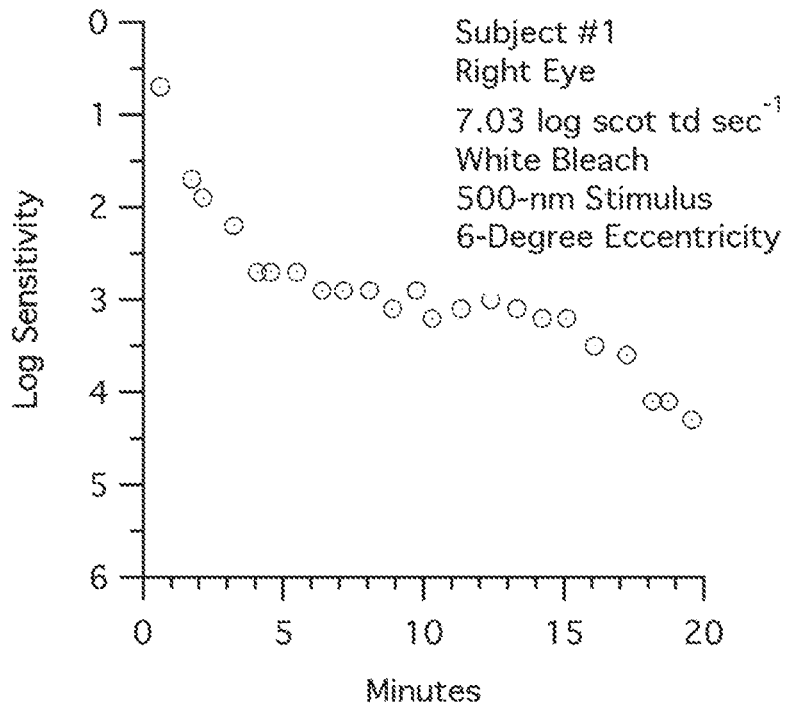
FIG. 4A shows a dark adaptation curve generated using a photobleaching light emitting an achromatic white light comprising a broad range of wavelengths from about 400 to about 700 nm.
Figure 4B:
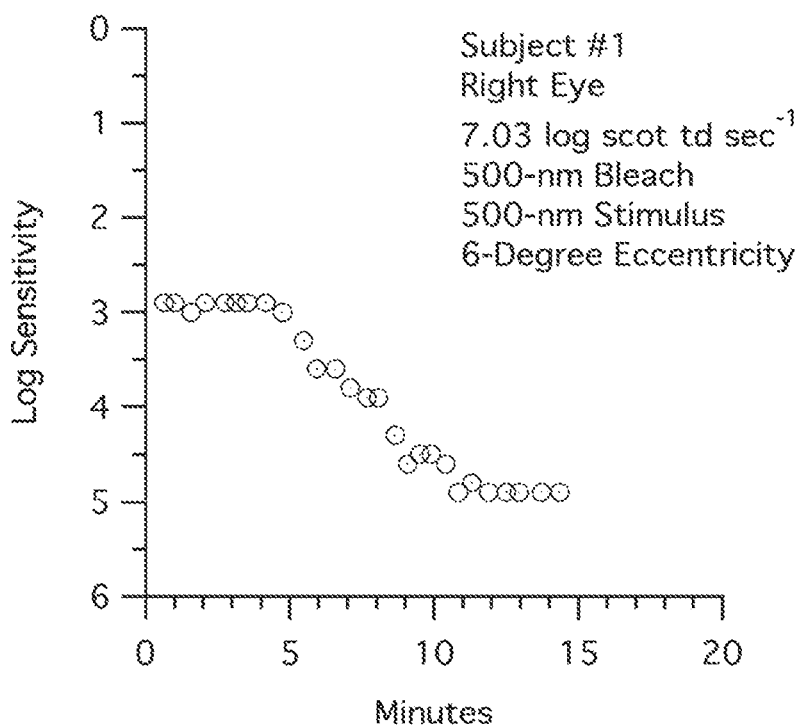
FIG. 4B shows a dark adaptation curve generated using a photobleaching light emitting a tailored spectrum of wavelengths centered on only the blue (about 405 nm to about 425 nm) spectrum.
Figure 4C:
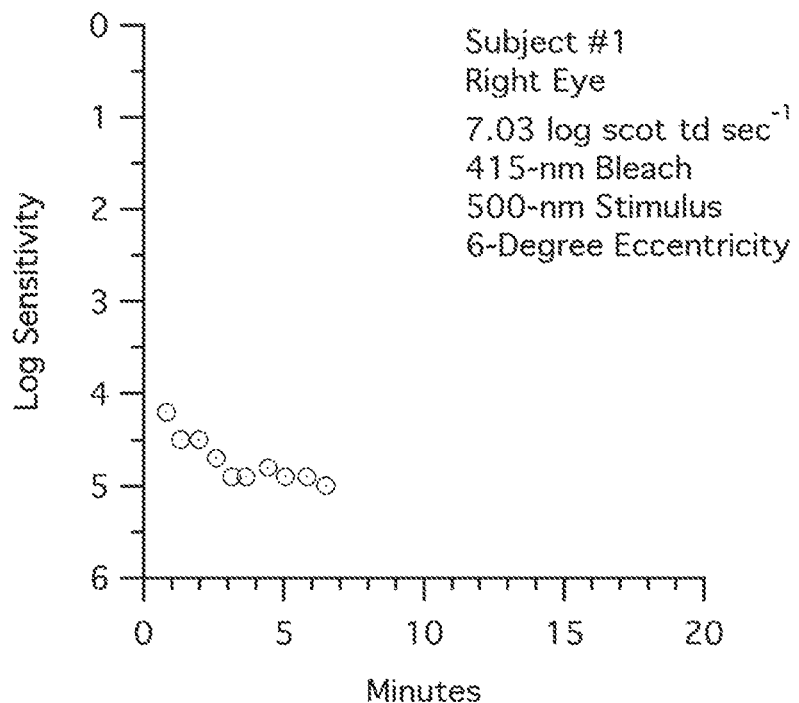
FIG. 4C shows a dark adaptation curve generated using a photobleaching light emitting a tailored spectrum of wavelengths centered on only the green (about 490 nm to about 510 nm) spectrum.
Figure 4D:
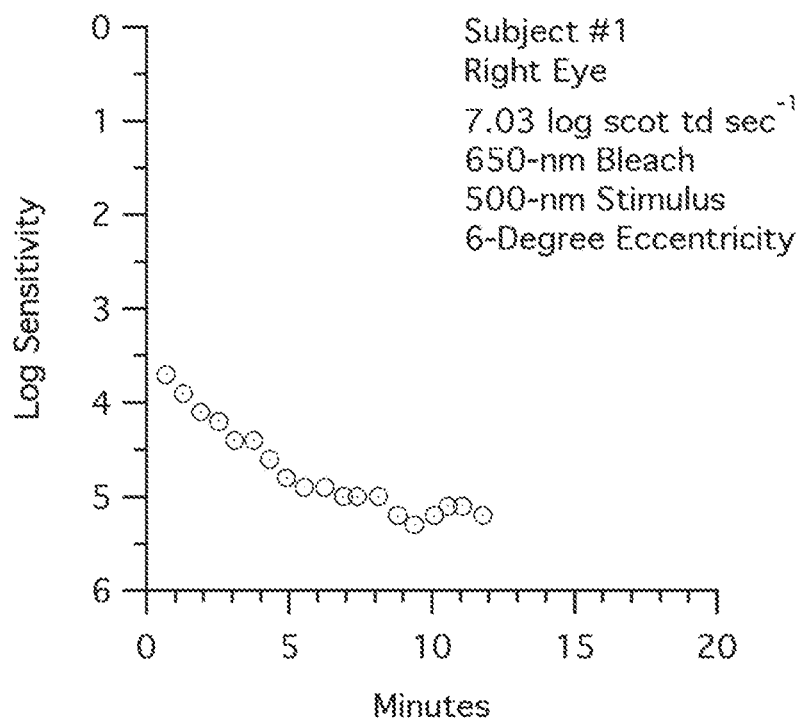
FIG. 4D shows a dark adaptation curve generated using a photobleaching light emitting a tailored spectrum of wavelengths centered on only the narrow red (about 640 nm to about 660 nm) spectrum.
Figure 6A:
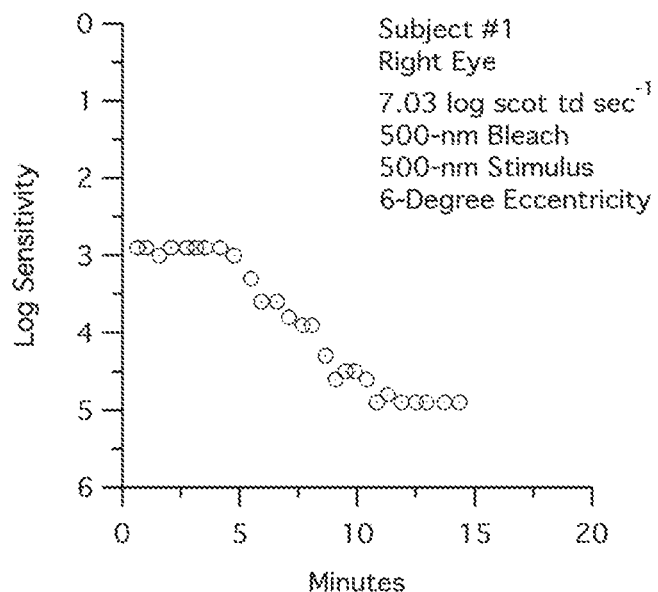
FIG. 6A shows a dark adaptation curve generated using a photobleaching light emitting a tailored spectrum of light consisting essentially of wavelengths of about 490 nm to about 510 nm (green spectrum).
Figure 6B:
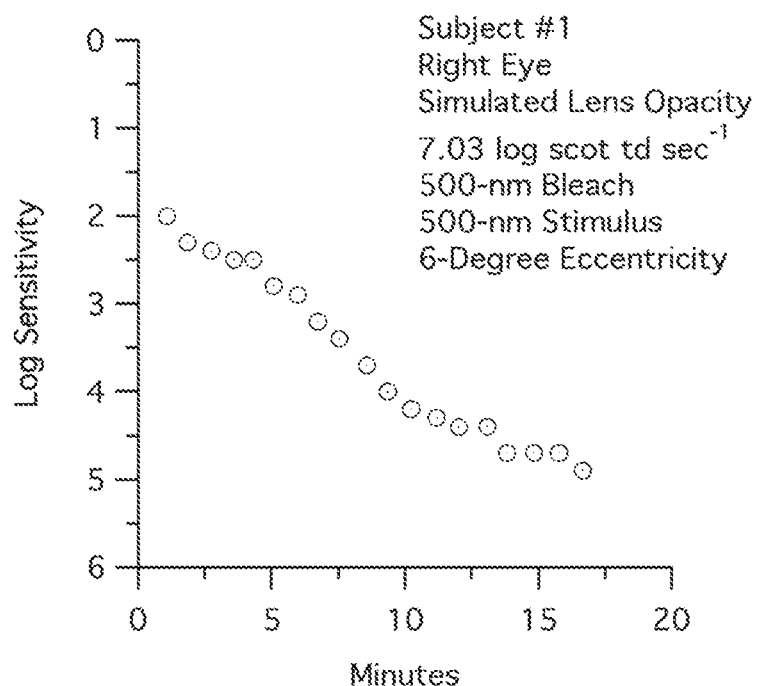
FIG. 6B shows a dark adaptation curve generated using a photobleaching light emitting a tailored spectrum of light consisting essentially of wavelengths of about 490 nm to about 510 nm (green spectrum) with the addition of a blue absorption filter placed in from of the test subject's eye.
Figure 6C:
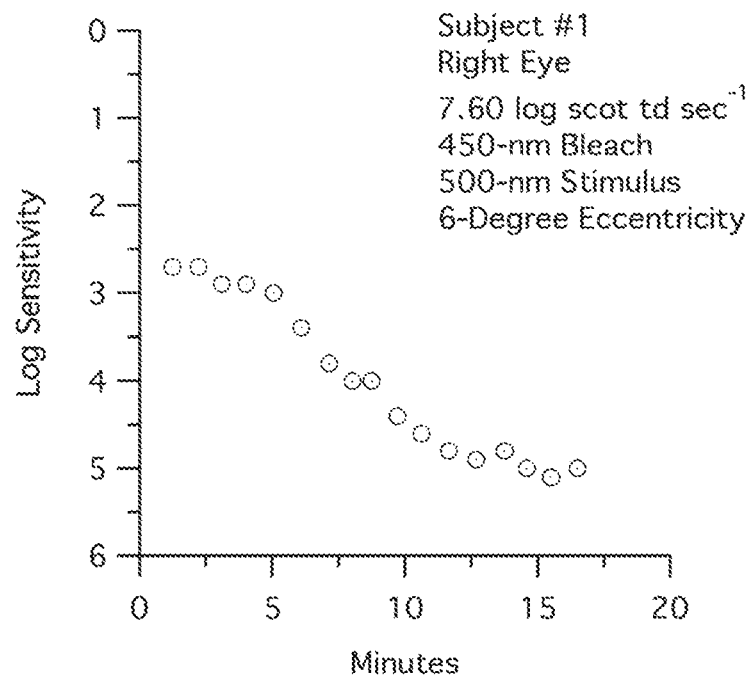
FIG. 6C shows a dark adaptation curve generated using a photobleaching light emitting a tailored spectrum of light consisting essentially of wavelengths of about 440 nm to about 460 nm (blue spectrum).
Figure 6D:
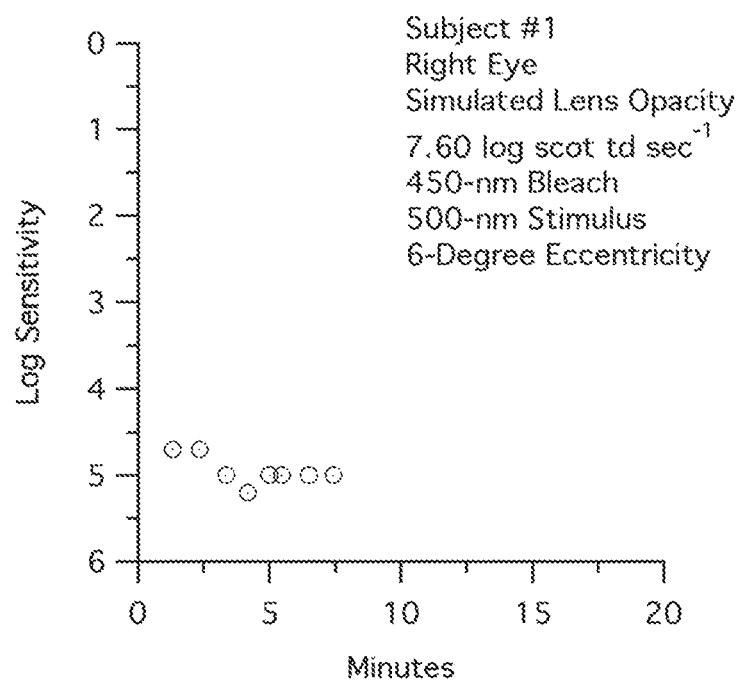
FIG. 6D shows a dark adaptation curve generated using a photobleaching light emitting a tailored spectrum of light consisting essentially of wavelengths of about 440 nm to about 460 nm (blue spectrum) with the addition of a blue absorption filter placed in from of the test subject's eye.

The intensity of the xenon arc photobleaching light (administered as a flash) incorporated in the dark adaptometer was set at 7.03 log scot Td sec$^{-1}$ and masked to photobleach an area of the retina covering about 4° of visual angle centered at 6° on the inferior vertical meridian. The spectrum of the photobleaching light was varied for each of four dark adaptation measurements. In one case, the photobleaching light emitted the essentially white, 5500 Kelvin color temperature broad spectrum light (consisting of wavelengths from about 400 nm to about 700 nm) generated by the xenon arc source (FIG. 4A). In the other three cases, the photobleaching light was tailored to emit a spectrum of light consisting essentially of wavelengths in the narrow blue (about 405 nm to about 425 nm), green (about 490 nm to about 510 nm) and narrow red (about 640 nm to about 660 nm) spectrums (FIGS. 4B-D, respectively). As used in the present the disclosure, the term "about" when used in reference to a wavelength or range of wavelengths it is meant to encompass a range of wavelengths on either side of the designated wavelength equal to the error in generation or measurement of the designated wavelength. The spectrums detailed above were generated by placing narrow bandpass interference filters (Edmund Optics NT43-158, NT43-169 and NT43-189, respectively) over the face of the xenon arc flash window. The test eye was photobleached while the subject was focused on a fixation light to ensure that the proper retinal location was bleached. Scotopic threshold measurements for the target stimulus began immediately after photobleach offset. The target stimulus was a circular spot covering about 2° of visual angle presented at 6° on the inferior vertical meridian with a wavelength spectrum centered on 500 nm. During threshold measurement the subject focused on the fixation light and responded when the stimulus was judged to be present by pushing a button. Threshold was estimated using a 3-down/1-up modified staircase procedure. Starting at a relatively high intensity (5.00 cd/m$^2$), the target was presented every 2 or 3 seconds for a 200-ms duration. If the subject did not respond the target stimulus was visible, the intensity of the target stimulus remained unchanged until the subject responded the target stimulus was visible. If the subject indicated the target stimulus was visible, the intensity of the target stimulus was decreased for each successive presentation in steps of 0.3 log units ("3-down") until the participant stopped responding that the target stimulus was present. After the subject indicated that the target stimulus was invisible by not pushing the button, the intensity of the target stimulus was increased for each successive presentation in steps of 0.1 log units ("1-up") until the subject responded that the target stimulus was once again visible. This intensity was defined as the threshold estimate. Successive threshold measurements were obtained starting with a target stimulus intensity 0.3 log units brighter than the previous threshold estimate. The subject had a 30-second rest period between threshold measurements. Threshold estimates were made about once a minute for the duration of the measurement protocol. About twenty threshold measurements were made during each dark adaptation test.

FIGS. 4A-D show four dark adaptation curves from the same test subject generated in response to the four different photobleaching light spectrums described above. The subject shows a stereotypical dark adaptation curve in response to the white photobleaching light as expected (FIG. 4A). Use of a photobleaching light tailored to emit a spectrum of light consisting essentially of wavelengths in the range of about 490 nm to about 510 nm (green spectrum), preserves the stereotypical shape of the dark adaptation function because the rods are still strongly bleached. In contrast, use of a photobleaching light tailored to emit a spectrum of light consisting essentially of wavelengths in the range of about 405 nm to about 425 nm (blue spectrum) (FIG. 4C) or a photobleaching light tailored to emit a spectrum of light consisting essentially of wavelengths in the range of about 640 nm to about 660 nm (red spectrum) (FIG. 4D) failed to produce a stereotypical dark adaptation response curve because the rods were only weakly photobleached. In addition, the dark adaptation response obtained using a photobleaching light tailored to emit a spectrum of light consisting essentially of wavelengths in the range of about 490 nm to about 510 nm (green spectrum) gave results more quickly than using a photobleaching light emitting a broad spectrum of light (compare FIGS. 4A and 4B). Recovery occurs faster because the additional photobleaching contribution from the blue and red components of the white spectrum, which is largely outside the rod response spectrum, has been eliminated.

Therefore, the use of a photobleaching light emitting a tailored spectrum of light consisting essentially of wavelengths in the range of about 490 nm to about 510 nm (green spectrum) was shown to give essentially the same dark adaptation response as a photobleaching light emitting a broad achromatic white bleach and to provide the results more quickly. This example shows that, for this particular objective (measuring dark adaptation), a photobleaching light emitting a tailored spectrum of light consisting essentially of wavelengths in the range of about 490 nm to about 510 nm (green spectrum) is an improvement over a photobleaching light emitting an achromatic broad spectrum of white light. However, it should be noted that for other objectives, the use a photobleaching light emitting a tailored spectrum of wavelengths other than that shown in this example may also be useful. In summary, essentially the same dark adaptation response is obtained with less patient burden, both because only a fraction of the total energy impinges on the retina and because the most irritating short wavelength portion of the spectrum is eliminated (i.e., the blue spectrum). Moreover, the result is obtained more quickly.

Example #2—Preference Test for White Flash Vs. Green Flash

In this example, a preference test was conducted comparing a photobleaching light comprising a broad wavelength spectrum of about 400 nm to about 700 nm generated by a xenon arc light and a photobleaching light that was tailored to emit a spectrum of light consisting essentially of wavelengths of about 490 nm to about 510 nm (green spectrum). These photobleaching light spectra were analyzed for their ability to generate classical dark adaptation curves in Example 1 above and shown to produce generally similar dark adaptation curves. The photobleaching light in each case was generated using a commercial camera flash system (SunPak 622 Super Pro). This system uses a xenon arc light source that generates a broad, relatively flat spectrum of light (5500 Kelvin color temperature) spanning the entire range of cone and rod sensitivity (about 400 nm to about 700 nm). The flash was set at its maximum intensity of 7.48 log scot Td sec$^{-1}$. The "green" flash was created by placing a narrow (about 490 nm to about 510 nm) bandpass interference filter (Edmund Optics; NT43-169) over the face of the xenon arc flash window. The broad wavelength "white" spectrum photobleaching light was created by placing a clear glass blank (essentially 100% transmittance at all wavelengths) over the face of the xenon arc flash window, so that the test subjects were confronted with similar configurations in both cases.

For each participant, one eye was exposed to the "white" photobleaching light comprising a broad wavelength spectrum of about 400 nm to about 700 nm and the opposite eye was exposed to the "green" photobleaching light that was tailored to emit a spectrum of light consisting essentially of wavelengths of about 490 nm to about 510 nm. The flash unit was held approximately 20 cm in front of the test eye, with the non-test eye covered. The right eye was always exposed to the photobleaching light first; however, the tests were counterbalanced with regard to sequence, alternating between the first flash being "white" photobleaching light with the properties described above and the first flash being "green" photobleaching light with the properties described above. There was an interval of approximately 1 minute between the two flashes. Immediately after exposure to each of the "white" and "green" photobleaching lights, the participants were asked to rate discomfort on a scale of 1 to 10, with 1 being "no discomfort, I would look at it all day" and 10 being "highly uncomfortable, I would not want to look at it again". At the conclusion of the entire sequence, the participants were asked if they had to be exposed to one of the "white" or "green" photobleaching lights again which of the two they would prefer.

A total of eleven naïve participants were tested. There were six females and five males, all Caucasian, with a mean age of 30.6 years (range 22 to 47). The age distributions (mean and range) for the two sexes were comparable. The results are shown in FIG. 5. There was a clear preference for the "green" photobleaching light, with an average rating of 2.8 for the "green" photobleaching light (range 1 to 5) vs. 5.1 for the "white" photobleaching light (range 2 to 8), and 91% of the subjects indicated a preference for the "green" photobleaching light if they were to be tested again. While the subpopulation numbers are small, there was a consistent preference for the "green" photobleaching light regardless of sex, age (under 30 vs. over 30) or the order of the "white"-"green" photobleaching light sequence. There was a tendency for young females to be more sensitive to the "white" photobleaching light and to show a stronger preference for the "green" photobleaching light.

Example 3—Effect of Photobleaching Light Spectrum on Variability in Dark Adaptation Measurements Due to Lens Opacity In this example, a comparison was made between dark adaptation curves generated using a photobleaching light that was tailored to emit a spectrum of light consisting essentially of wavelengths of about 490 nm to about 510 nm (green spectrum) and a photobleaching light that was tailored to emit a spectrum of light consisting essentially of wavelengths of about 440 nm to about 460 nm (blue spectrum), both with and without a blue absorption filter in front of the test subject's eye. The blue absorption filter simulates the preferential absorption of shorter wavelengths due to lens opacity.

Dark adaptation functions were measured using an AdaptDx dark adaptometer (Apeliotus Technologies, Inc.) as described in Example 1 above as modified below. To generate the photobleaching light with the green spectrum, the intensity of the xenon arc light source incorporated in the dark adaptometer was set at 7.03 log scot Td sec$^{-1}$, and a narrow green (about 490 nm to about 510 nm) bandpass interference filter (Edmund Optics NT43-169) was placed over the face of the xenon arc flash window. To generate the photobleaching light with the blue spectrum, the intensity of the xenon arc light source incorporated in the dark adaptometer was set at 7.60 log scot Td sec$^{-1}$, and a narrow blue (about 440 nm to about 460 nm) bandpass interference filter (Edmund Optics NT43-163) was placed over the face of the xenon arc flash window. FIGS. 6A-D show the resulting dark adaptation functions. Placing the blue absorption filter in front of the test subject's eye to lower the transmission of short-wavelength light in a fashion similar to that encountered with lens opacity, such as caused by cataracts and age-related increases in lens opacity, had minimal impact on the dark adaptation curves generated using the green spectrum photobleaching light (compare FIG. 6A, designated control, vs. FIG. 6B, designated simulated lens opacity). Conversely, the simulated lens opacity had a major impact on the dark adaptation curves generated using the blue spectrum photobleaching light (compare FIG. 6C, designated control, vs. FIG. 6D, designated simulated lens opacity).

These results show that the use of a photobleaching light tailored to emit a spectrum of light consisting essentially of wavelengths of about 490 nm to about 510 nm (green spectrum) minimizes the variability in dark adaptation responses, and associated diagnostic measurements, due to the filtering effects of lens opacity, such as caused by cataracts and age-related increases in lens opacity.

Example 4—Photobleaching Below Ambient Daylight Levels

In this example, a comparison was made between dark adaptation curves generated using a photobleaching light having an intensity above the intensity of ambient daylight and a photobleaching light having an intensity below the intensity of ambient daylight. Dark adaptation speed was determined using a sensitive and reliable benchmark known as the rod intercept. The rod intercept is the time for scotopic sensitivity to recover to $5 \times 10^{-4}$ cd/m$^2$.

Figure 7A:
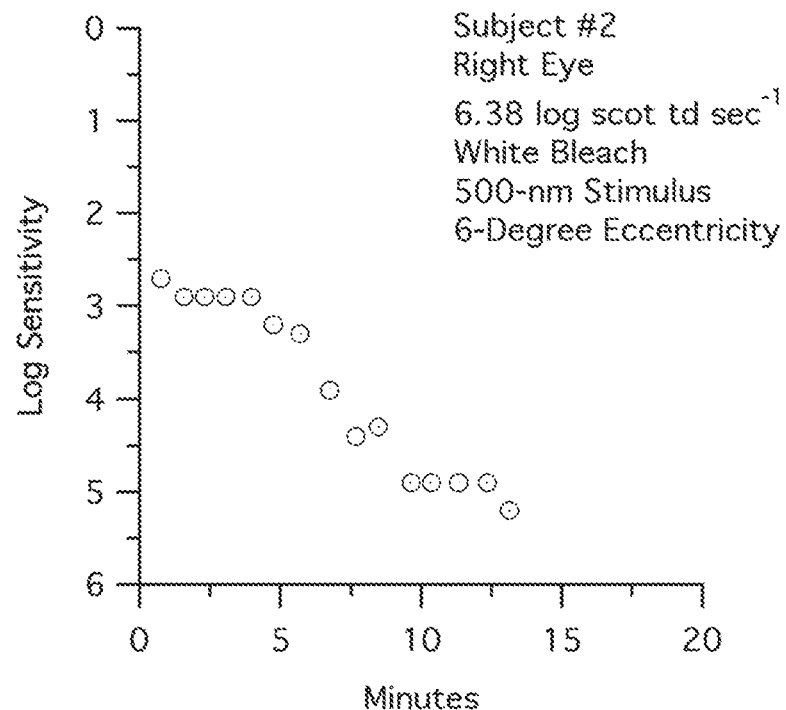
FIG. 7A shows a dark adaptation curve generated using a bright, achromatic white photobleaching light having an intensity above the intensity of ambient daylight.
Figure 7B:
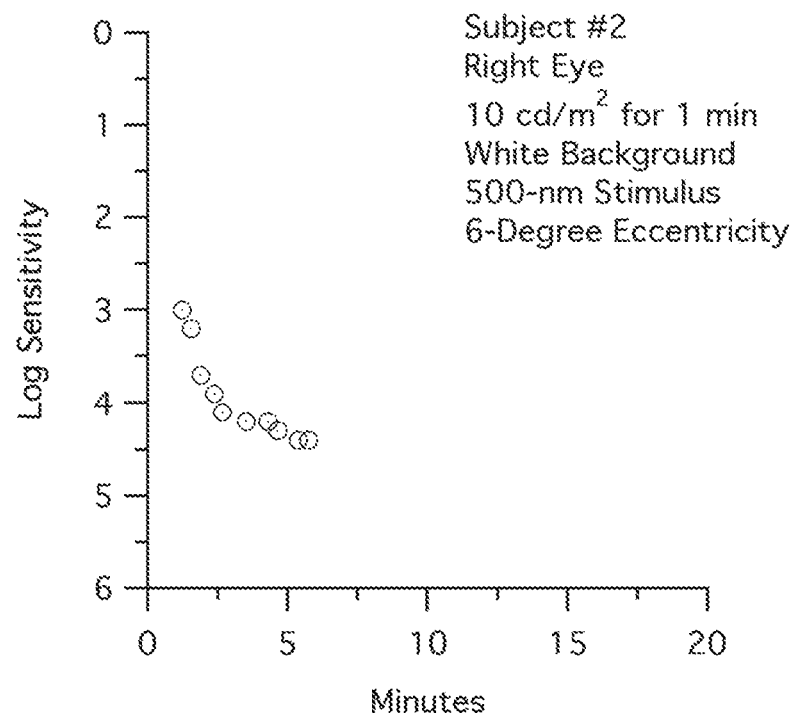
FIG. 7B shows a dark adaptation curve generated using a dim (uniform bleaching field having an intensity below the intensity of ambient daylight.

Dark adaptation functions were measured using an AdaptDx dark adaptometer (Apeliotus Technologies, Inc.) as described in Example 1 above as modified below. Dark adaptation curves were generated using methods known in the art. FIG. 7 compares two dark adaptation curves from the same test subject. In the first case (FIG. 7A), photobleaching was accomplished using a bright, achromatic white flash photobleach generated by a xenon arc light source producing a broad, relatively flat spectrum of light (5500 Kelvin color temperature) spanning the entire range of cone and rod sensitivity and having an intensity of 6.38 log scot Td sec$^{-1}$, which is well above the intensity of ambient daylight. In the second case (FIG. 7B) photobleaching was accomplished using with a dim (10 cd/m$^2$) uniform bleaching field for 1-minute, which is well below the intensity of ambient daylight levels. The rod intercept in response to the bright, achromatic white flash photobleach was 6.97 minutes compared with 2.54 minutes for the dim background photobleaching. The cone-mediated portion of the dark adaptation function (the first four thresholds in FIG. 7A) is effectively eliminated by using the dim photobleaching procedure. Thus, use of a photobleaching light having an intensity less than the intensity of ambient daylight can dramatically shorten the duration of a dark adaptation test.

Example 5—Effect of Eccentricity on Dark Adaptation in Age-Related Maculopathy

In this example, a comparison was made between dark adaptation curves generated by measuring dark adaptation at positions 5° and 12° on the inferior vertical meridian, using both normal test subjects and test subjects with age-related maculopathy (ARM).

Dark adaptation functions were measured using an AdaptDx dark adaptometer (Apeliotus Technologies, Inc.) as described in Example 1 above as modified below. Dark adaptation function was measured in response to a 4° diameter photobleaching light (provided as a flash) with an intensity of 6.38 log scot Td sec$^{-1}$. In this example, the photobleaching light was the essentially white, 5500 Kelvin color temperature broad spectrum light (having wavelengths from about 400 nm to about 700 nm) generated by the xenon arc source incorporated in the dark adaptometer. The target stimulus light was a 2° diameter, 500-nm circular spot centered within the area subjected to photobleaching. Scotopic threshold measurements began immediately after photobleach offset. During threshold measurement the subject focused on the fixation light and responded when the stimulus was judged to be present by pushing a button. Threshold was estimated using a 3-down/1-up modified staircase procedure. Approximately one threshold was measured each minute for 20 minutes. Dark adaptation speed was determined using a sensitive and reliable benchmark known as the rod intercept. The rod intercept is the time for scotopic sensitivity to recover to $5 \times 10^{-4}$ cd/m$^2$. The dark adaptation impairment of the ARM patients was calculated relative to a control group of age-matched adults.

Anatomical studies have shown that the area of greatest rod dysfunction associated with ARM is within the parafoveal region (3° to 5° eccentricity) of the retina. The pattern of scotopic sensitivity impairment exhibited by ARM patients is consistent with the anatomical findings; that is, scotopic sensitivity impairment is greatest in the parafoveal region and decreases as a function of eccentricity towards the retinal periphery. In this example, we examined whether dark adaptation impairment has a similar pattern of dysfunction.

A total of 5 normal old adults and 8 ARM patients were tested. Group assignment was based on grading of fundus photographs using the AREDS AMD Severity Classification System. Best-corrected visual acuity (ETDRS chart) and contrast sensitivity (Pelli-Robson chart) were measured on the day of testing. Dark adaptation function was measured as described above. Each participant had their dark adaptation function measured on the inferior vertical meridian at 5° and 12° on separate testing days. Both groups were similar in age, test eye acuity, and test eye contrast sensitivity. Dark adaptation impairment for the AMD group relative to the normal old adults was almost 5 minutes greater at 5° than it was at 12°. Furthermore, for the AMD group dark adaptation was almost 3 minutes slower at 5° than at 12° for the AMD group, whereas for the normal old adults dark adaptation was almost 3 minutes faster at 5° than at 12°.

Patients in the ARM group exhibit greater dark adaptation impairment in the parafoveal region compared to an area adjacent to the macula. In general, the AMD group's dark adaptation was slower in the parafoveal region compared with the more peripheral point; whereas, the normal old adults exhibited the opposite pattern. These results show that tailoring the region of the retina that is subject to photobleaching and subsequent testing to the pattern of dysfunction for a particular disease, for example, by choosing a region of the retina with maximum disease susceptibility, or by comparison of one or more areas having different disease susceptibilities in a single test, may be useful in the design of a diagnostic aimed at detecting the earliest stages of a disease. While this principle was illustrated in the current example using ARM, it is equally applicable to other disease states.

Example 6—Effect of Photobleaching Light Spectrum on Detection of Age-Related Maculopathy In this example, a comparison was made between dark adaptation curves generated by measuring dark adaptation with achromatic and green photobleaching lights, using both normal test subjects and test subjects with age-related maculopathy (ARM).

Figure 8A:
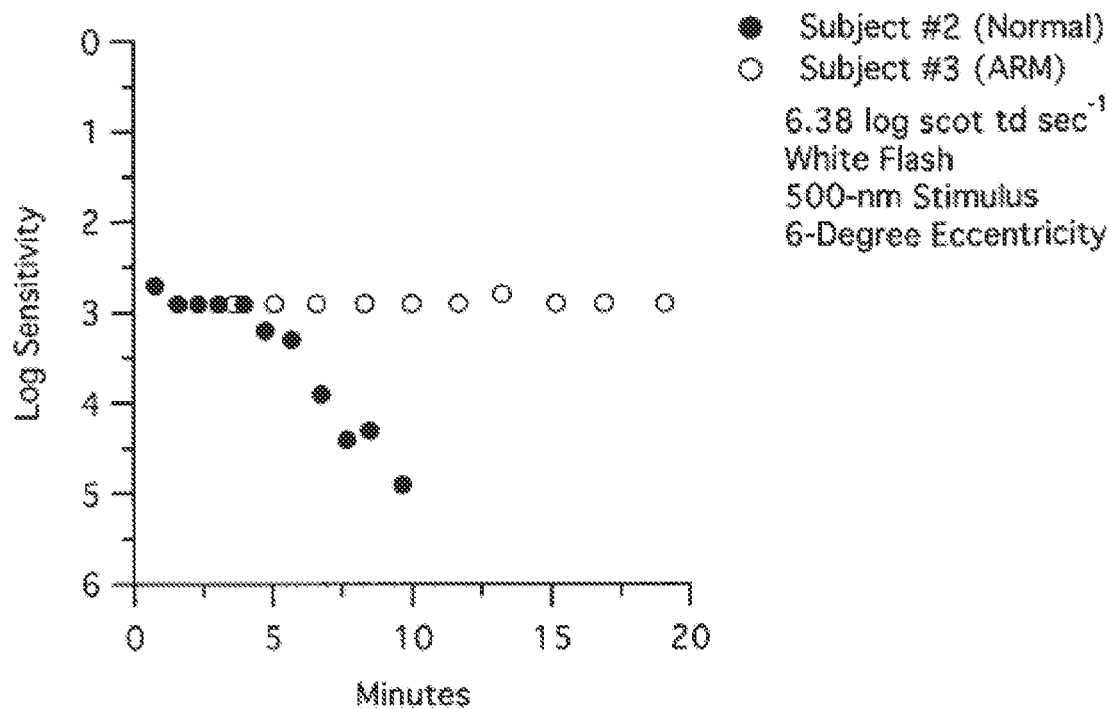
FIG. 8A shows a dark adaptation curve generated using a photobleaching light emitting an achromatic white light comprising a broad wavelength spectrum of about 400 to about 700 nm for both normal test subjects and test subjects having age-related maculopathy (ARM).
Figure 8B:
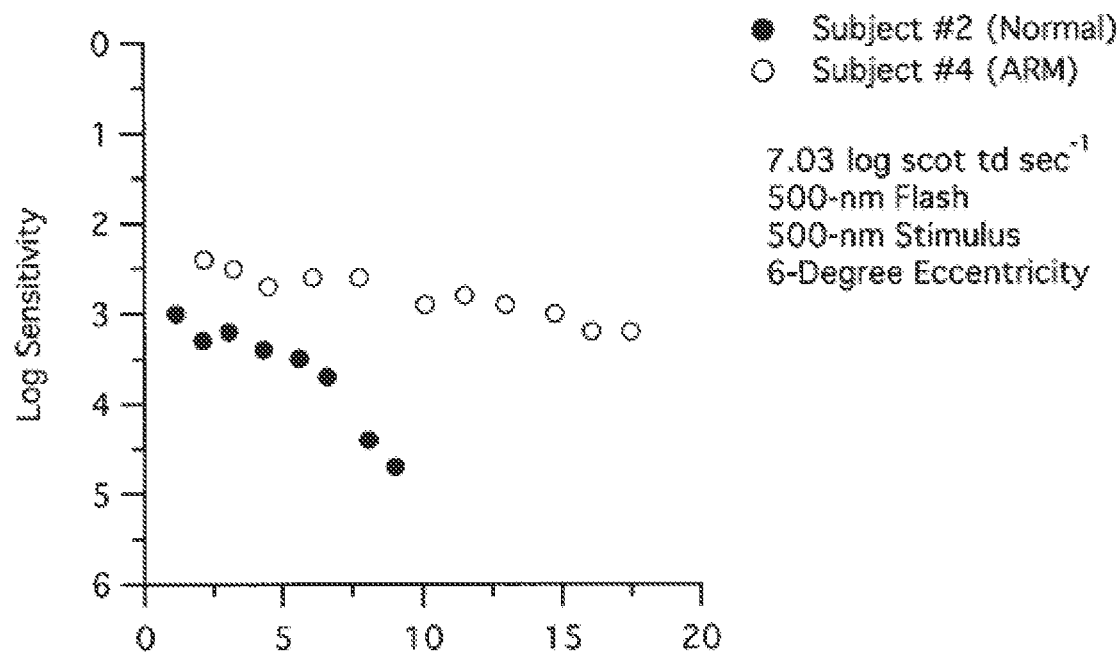
FIG. 8B shows a dark adaptation curve generated a photobleaching light emitting a tailored spectrum of light consisting essentially of wavelengths of about 490 nm to about 510 nm (green spectrum) for both normal test subjects and test subjects having age-related maculopathy (ARM).

Dark adaptation functions were measured using an AdaptDx dark adaptometer (Apeliotus Technologies, Inc.) as described in Example 1 above as modified below. In one case, an achromatic bleaching light (essentially white, 5500 Kelvin color temperature broad spectrum consisting of wavelengths from about 400 nm to about 700 nm) was generated by the xenon arc light source incorporated in the dark adaptometer, with the intensity of the flash set at 6.38 log scot Td sec$^{-1}$ (FIG. 8A). In the other case, a green bleaching light (about 490 nm to about 510 nm) was generated by placing a narrow green bandpass interference filter (Edmund Optics NT43-169) over the face of the xenon arc flash incorporated in the dark adaptometer, with the intensity of the flash set at 7.03 log scot Td sec$^{-1}$ (FIG. 8B). These two conditions produce nearly equivalent photobleaching of the photoreceptor visual pigments.

In both cases a normal adult and an ARM patient were tested. The response patterns for the achromatic and green photobleaching lights are the same, with the ARM patient exhibiting markedly slowed dark adaptation relative to the normal adult in both cases. Jackson and Edwards (A Short-Duration Dark Adaptation Protocol for Assessment of Age-belated Maculopathy, Journal of Ocular Biology, Diseases, and Informatics; in press 2008, incorporated herein in its entirety by reference) have shown that measurement of dark adaptation using an achromatic photobleaching light is a sensitive and specific diagnostic for ARM. The results of this example show that the ability to discriminate ARM is preserved when using a green bleaching light, allowing the added benefit of lower patient burden and lower confound from lens opacity without loss of diagnostic utility.

The foregoing description illustrates and describes the methods and other teachings of the present disclosure. Additionally, the disclosure shows and describes only certain embodiments of the methods and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain best modes known of practicing the methods and other teachings of the present disclosure and to enable others skilled in the art to utilize the teachings of the present disclosure in such, or other, embodiments and with the various modifications required by the particular applications or uses. Accordingly, the methods and other teachings of the present disclosure are not intended to limit the exact embodiments and examples disclosed herein. All references cited herein are incorporated by reference as if fully set forth in this disclosure.

What is claimed:

1. An apparatus for measuring an ability of an eye of a test subject to adapt to darkness using a series of responses, received from the test subject over a period of time, which indicate the test subject's observation of a stimulus light beam after exposure to a photobleaching light beam, the apparatus comprising:
a housing comprising:
a viewing opening;
a photobleaching light source configured to generate the photobleaching light beam, the photobleaching light beam having a tailored wavelength spectra spanning within a spectrum visible to human eye;
a stimulus light source configured to generate the stimulus light beam for stimulating the eye of the test subject; and
a display configured to:
a) display a bleach spot generated by the photobleaching light source and direct the photobleaching light beam to the eye of the test subject to photobleach one or more photoreceptors of the eye; and
b) display a stimulus spot generated by the stimulus light source and direct the stimulus light beam to the eye of the test subject.

2. The apparatus of claim 1, wherein the tailored wavelength spectra comprises wavelengths in a green spectrum.

3. The apparatus of claim 2, wherein the tailored wavelength spectra comprises a range of wavelengths from 490 nm to 510 nm.

4. The apparatus of claim 3, wherein the bleach spot comprises a green flash.

5. The apparatus of claim 3, wherein the photobleaching light source comprises an LED light source.

6. The apparatus of claim 3, wherein the photobleaching light source comprises an OLED light source.

7. The apparatus of claim 3, wherein the photobleaching light source comprises a photographic flash.

8. The apparatus of claim 3, wherein the display comprises a plasma display.

9. The apparatus of claim 3, wherein the display comprises a LED display.

10. The apparatus of claim 3, wherein the bleaching spot is larger than the stimulus spot.

11. The apparatus of claim 10, wherein the stimulus spot comprises a circular spot.

12. The apparatus of claim 11, wherein the stimulus light source is configured to control intensity of the stimulus light.

13. The apparatus of claim 12, wherein the display is configured to display the stimulus light at varying intensity levels.

14. The apparatus of claim 13, wherein the display is configured to display the stimulus light at varying locations.

15. The apparatus of claim 14, wherein the display is configured to display the stimulus light at a first intensity until a response indicating the subject's observation of the stimulus light beam is received.

16. The apparatus of claim 14, wherein the display is configured to increase intensity level of the stimulus light until a response indicating the subject's observation of the stimulus light beam is received.

17. The apparatus of claim 15, wherein the display is configured to display the stimulus light at a second intensity after the response indicating the subject's observation of the stimulus light beam is received, wherein the second intensity is lower than the first intensity.

18. The apparatus of claim 15, wherein the display is configured to display the stimulus spot every 2 seconds.

19. The apparatus of claim 15, wherein the display is configured to display the stimulus spot every 3 seconds.

20. The apparatus of claim 15, wherein the display is configured to display the stimulus spot for a 200 millisecond duration.

21. The apparatus of claim 15, wherein the display is further configured to display a fixation light.

22. The apparatus of claim 21, wherein the display is configured to display the bleach spot while displaying the fixation light.

23. The apparatus of claim 22, wherein the stimulus light comprises a range of wavelengths centered at 505 nm.

24. The apparatus of claim 22, wherein the stimulus light comprises a range of wavelengths centered at 450 nm.

25. The apparatus of claim 1, wherein the viewing opening is configured to receive a head of the test subject.

* * * * *